(12) United States Patent
Milligan et al.

(10) Patent No.: US 8,058,421 B2
(45) Date of Patent: Nov. 15, 2011

(54) PROMOTERS FOR REGULATION OF GENE EXPRESSION IN PLANT ROOTS

(75) Inventors: Stephen B. Milligan, Kirkland, WA (US); Dale Skalla, Research Triangle Park, NC (US); Kay Lawton, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/689,321

(22) Filed: Jan. 19, 2010

(65) Prior Publication Data

US 2010/0205693 A1  Aug. 12, 2010

Related U.S. Application Data

(62) Division of application No. 10/490,147, filed as application No. PCT/US02/35374 on Nov. 4, 2002, now Pat. No. 7,674,893.

(60) Provisional application No. 60/337,026, filed on Nov. 7, 2001.

(51) Int. Cl.
*C12N 15/82* (2006.01)
*C12N 5/04* (2006.01)
*C07H 21/04* (2006.01)
*A01H 5/00* (2006.01)

(52) U.S. Cl. ............. 536/24.1; 435/320.1; 435/419; 800/298

(58) Field of Classification Search .............. None
See application file for complete search history.

(56) References Cited

U.S. PATENT DOCUMENTS

| | | | |
|---|---|---|---|
| 5,459,252 A * | 10/1995 | Conkling et al. | 800/302 |
| 5,466,785 A | 11/1995 | de Framond | |
| 5,633,363 A | 5/1997 | Colbert et al. | |
| 5,750,386 A | 5/1998 | Conkling et al. | |
| 5,837,848 A | 11/1998 | Ely et al. | |
| 6,018,099 A | 1/2000 | de Framond | |
| 6,194,636 B1 | 2/2001 | McElroy et al. | |
| 6,207,879 B1 | 3/2001 | McElroy et al. | |
| 6,232,526 B1 | 5/2001 | McElroy et al. | |

FOREIGN PATENT DOCUMENTS

| | | |
|---|---|---|
| EP | 1033405 A2 | 9/2000 |
| WO | 0029594 | 5/2000 |
| WO | 200053763 A1 | 9/2000 |
| WO | 0119976 | 3/2001 |
| WO | 0168911 A2 | 9/2001 |
| WO | 0183790 | 11/2001 |

OTHER PUBLICATIONS

Kim Y. et al. A 20 nucleotide upstream element is essential for the nopaline synthase (nos) promoter activity. Plant Mol Biol. Jan. 1994;24(1):105-17.
Verdaguer B. et al. Functional organization of the cassava vein mosaic virus (CsVMV) promoter. Plant Mol Biol. Aug. 1998;37(6):1055-67.
De Boer G. et al. Sequences surrounding the transcription initiation site of the *Arabidopsis enoyl-acyl* carrier protein reductase gene control seed expression in transgenic tobacco. Plant Mol Biol. Apr. 1999;39(6):1197-207.
Hwang and Goodman, "An *Arabidopsis thaliana* root-specific kinase homolog is induced by dehydration, ABA and NaCI," The Plant Journal, (1995), 8(1), pp. 37-43.
Lu and Bruce, "A Novel Cis-Acting Element Conferring Root-Preferred Gene Expression in Maize," J. Plant Physiol., vol. 156, No. 2, Feb. 2000, pp. 277-283.
Database EMBL [online], "Z.mays MRNA for b-32 protein, putative regulatory factor of zein expression (clone b-32.129)," Feb. 10, 2003, Retrieved from EBI accession No. EM.sub.—PRO:ZMB32129, Database accession No. ZMB32129.
Database Genseq on STIC, Thomson Derwent, (London, UK), Accession No. AAA97280, RITCHIE, gene sequence, Jan. 16, 2001.
Database Genseq on STIC, Thomson Derwent, (London, UK), Accession No. AAF81466, Anderson et al., Gene Sequence, Jun. 8, 2001.
Database Genseq on STIC, Thomson Derwent, (London, UK), Accession No. AAS96577, Conner et al., Gene Sequence, Feb. 26, 2002.
Database Genseq on STIC, Thomson Derwent, (London, UK), Accession No. AAC41277, Gene Sequence, Oct. 17, 2000.
Database Genseq on STIC, National Center for Biotechnology Information, (Bethesda, MD, USA), Accession No. AW313195, WALBOT, Gene Sequence, Jan. 24, 2000.

* cited by examiner

*Primary Examiner* — Cynthia Collins
(74) *Attorney, Agent, or Firm* — Bruce Vrana

(57) ABSTRACT

The present invention is directed to promoters isolated from maize and functional equivalents thereto. The promoters of the present invention have particular utility in driving root-specific expression of heterologous genes that impart increased agronomic, horticultural and/or pesticidal characteristics to a given transgenic plant. The present invention is also drawn to DNA molecules comprising the promoters of the invention and transformed plant tissues containing DNA molecules comprising a promoter of the invention operably linked to a heterologous gene or genes, and seeds thereof.

10 Claims, No Drawings

PROMOTERS FOR REGULATION OF GENE EXPRESSION IN PLANT ROOTS

CROSS-REFERENCE TO RELATED APPLICATIONS

This application is a divisional of U.S. patent application Ser. No. 10/490,147, incorporated herein in its entirety, which is a National Stage Entry of PCT/US02/35374.

FIELD OF THE INVENTION

The present invention relates generally to the field of plant molecular biology and the regulation of gene expression in plants. More specifically, the present invention relates to the regulation of gene expression in plant roots.

BACKGROUND OF THE INVENTION

Manipulation of crop plants to alter and/or improve phenotypic characteristics (such as productivity or quality) requires the expression of heterologous genes in plant tissues. Such genetic manipulation has become possible by virtue of two discoveries: the ability to transform heterologous genetic material into a plant cell and by the existence of promoters that are able to drive the expression of the heterologous genetic material.

It is advantageous to have the choice of a variety of different promoters so as to give the desired effect(s) in the transgenic plant. Suitable promoters may be selected for a particular gene, construct, cell, tissue, plant or environment. Promoters that are useful for plant transgene expression include those that are inducible, viral, synthetic, constitutive (Odell et al., 1985, Nature 313: 810-812; Granger & Cyr, 2001, Plant Cell Repo. 20: 227-234), temporally regulated, spatially regulated, tissue-specific, and spatio-temporally regulated (Kuhlemeier et al. 1987, Ann. Rev. Plant Physiol. Plant Mol. Biol. 38: 221-257). Promoters from bacteria, fungi, viruses and plants have been used to control gene expression in plant cells.

Promoters consist of several regions that are necessary for full function of the promoter. Some of these regions are modular, in other words they can be used in isolation to confer promoter activity or they may be assembled with other elements to construct new promoters. The first of these promoter regions lies immediately upstream of the coding sequence and forms the "core promoter region" containing consensus sequences, normally 20-70 base pairs immediately upstream of the coding sequence. The core promoter region contains a TATA box and often an initiator element as well as the initiation site. The precise length of the core promoter region is not fixed but is usually well recognizable. Such a region is normally present, with some variation, in most promoters. The base sequences lying between the various well-characterized elements appear to be of lesser importance. The core promoter region is often referred to as a minimal promoter region because it is functional on its own to promote a basal level of transcription.

The presence of the core promoter region defines a sequence as being a promoter: if the region is absent, the promoter is non-functional. The core region acts to attract the general transcription machinery to the promoter for transcription initiation. However, the core promoter region is insufficient to provide full promoter activity. A series of regulatory sequences, often upstream of the core, constitute the remainder of the promoter. The regulatory sequences determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

Frequently, it is desirable to have tissue-specific expression of a gene of interest in a plant. Tissue-specific promoters promote expression exclusively in one set of tissues without expression throughout the plant; tissue-preferred promoters promote expression at a higher level in a subset of tissues with significantly less expression in the other tissues of the plant. For example, one may desire to express a value-added product only in corn seed but not in the remainder of the plant. Another example is the production of male sterility by tissue-specific ablation. In this case, a phytotoxic product is expressed only in the male tissue of the plant to ablate that specific tissue while other tissues of the flower as well as the rest of the plant remain intact. Many aspects of agricultural biotechnology use and require tissue-specific expression.

One important example of a need for promoters is for the expression of selected genes in plant roots. The plant root consists of many cell types such as epidermal, root cap, columella, cortex, pericycle, vascular and root hair forming trichoblasts, organized into tissues or regions of the root, for example, the root tip, root epidermis, meristematic zone, primary root, lateral root, root hair, and vascular tissue. Promoters isolated as root-specific or root-preferred can be biased towards promotion of expression in one or a few of these cell types. This cell-specific activity can be useful for specific applications such as regulating meristematic activity in only the meristematic cell zone or expression of a nematicidal gene in only the cell types that are contacted by the nematode pest. In other cases, broader cell-type specificity may be desired to express genes of interest throughout the root tissue. This may be useful in expressing an insecticidal gene to control an insect pest that feeds on plant roots, for instance corn rootworm (*Diabrotica* spp.). Broader cell-type root specificity may be accomplished with a single root-specific promoter with broad cell-type specificity or by using two or more root-specific or root-preferred promoters of different cell-type specificities for expression. A limited number of examples of root-preferred and root-specific promoters have been described. These include the RB7 promoter from *Nicotiana tabacum* (U.S. Pat. Nos. 5,459,252 and 5,750,386); the ARSK1 promoter from *Arabidopsis thaliana* (Hwang and Goodman (1995) Plant J 8:37-43), the MR7 promoter from *Zea mays* (U.S. Pat. No. 5,837,848), the ZRP2 promoter of *Zea mays* (U.S. Pat. No. 5,633,363), and the MTL promoter from *Zea mays* (U.S. Pat. Nos. 5,466,785 and 6,018,099). Many of these examples disclose promoters with expression patterns confined to a limited number of root tissues. Others fail to provide the root-specificity needed for expression of selected genes. Thus, there is a need in the art for isolation and characterization of new root promoters to obtain those of different breadth, expression level and specificity of cell-type expression for root-specific and root-preferred expression, particularly for root-specific expression.

SUMMARY OF THE INVENTION

Within the present invention, compositions and methods for directing root-specific expression in transgenic plants are provided. In particular, novel nucleic acid molecules isolated from *Zea mays*, that drive expression of heterologous genes in a root-specific manner in plants, are provided. The invention is further drawn to expression cassettes and vectors comprising the novel nucleic acid molecules of the invention operably linked to heterologous coding sequences. The invention is still further drawn to transgenic plants comprising the expression cassettes of the invention. The present invention also provides methods for specifically expressing a heterologous coding sequence in transgenic plant roots, for isolating a root-specific cDNA, for isolating a nucleic acid molecule useful for directing root-specific expression and for isolating a root-specific promoter. The invention further provides primers and nucleic acid probes to identify related nucleotide sequences from other plant genomes that direct root-specific or root-preferred transcription.

According to one aspect, the present invention provides an isolated nucleic acid molecule which codes for a promoter capable of directing root-specific transcription in a plant, wherein the nucleotide sequence of the promoter comprises a nucleotide sequence selected from the group consisting of: (a) a nucleotide sequence of SEQ ID NO: 1, SEQ ID NO: 2, SEQ ID NO: 3, or SEQ ID NO: 4; (b) a nucleotide sequence that hybridizes under high stringency conditions to a nucleotide sequence of a); and (c) a nucleotide sequence comprising a fragment of a sequence of (a), wherein the fragment maintains function of the nucleotide sequence of (a).

In another aspect, the present invention provides fragments of the nucleotide sequences set forth in SEQ ID NOS: 1-4 wherein the fragments code for promoters capable of directing root-specific transcription in a plant. In a preferred embodiment of this aspect, the fragments are made by making 5'-deletions in the nucleotide sequences set forth in SEQ ID NOS: 1-4. More preferably the fragment is a 5'-deletion of the nucleotide sequence set forth in SEQ ID NO: 1 or SEQ ID NO: 2.

The present invention also provides an expression cassette comprising the nucleic acid molecule of the invention operably linked to a heterologous coding sequence. In one embodiment, the expression cassette comprises a heterologous coding sequence selected from the group consisting of insecticidal coding sequences, nematicidal coding sequences, herbicide-tolerance coding sequences, anti-microbial coding sequences, anti-fungal coding sequences, anti-viral coding sequences, abiotic stress tolerance coding sequences, nutritional quality coding sequences, visible marker coding sequences and selectable marker coding sequences. In a preferred embodiment, the expression cassette comprises an insecticidal coding sequence that encodes a toxin active against a coleopteran pest. In a preferred aspect of this embodiment, the coleopteran pest is a species in the genus *Diabrotica*. In yet another embodiment, the expression cassette comprises an abiotic stress tolerance coding sequence including but not limited to drought stress, nutrient stress, salt stress, water stress and heavy metal stress. In still another embodiment, the expression cassette comprises a visible marker coding sequence including but not limited to green fluorescent protein (GFP), β-glucuronidase (GUS), and luciferase (LUC). In yet another embodiment, the expression cassette comprises a selectable marker coding sequence including but not limited to phosphomannose isomerase (PMI), an antibiotic resistance gene such as hygromycin, kanamycin and the like, a herbicide tolerance gene such as phosphinothricin and the like and barnase (bar).

The present invention also provides a recombinant vector comprising the expression cassette of the invention. In a preferred embodiment, the recombinant vector is a plasmid.

Further, the present invention provides a transgenic non-human host cell comprising the expression cassette of the invention. A transgenic host cell according to this aspect of the invention is preferably a plant cell. Even further, the present invention provides a transgenic plant comprising such a transgenic plant cell. A transgenic plant according to this aspect of the invention may be sorghum, wheat, sunflower, tomato, cole crops, cotton, rice, soybean, sugar beet, sugarcane, tobacco, barley, oilseed rape and maize, preferably maize or rice. Still further, the present invention provides transgenic seed from the group of transgenic plants consisting of sorghum, wheat, sunflower, tomato, cole crops, cotton, rice, soybean, sugar beet, sugarcane, tobacco, barley, oilseed rape and maize. In a particularly preferred embodiment, the transgenic seed is from a transgenic maize plant or rice plant.

In another aspect, the present invention provides a method of specifically expressing a heterologous coding sequence in transgenic plant roots under transcriptional control of a nucleic acid molecule of the invention, comprising: (a) transforming plant cells with a vector wherein the vector comprises the nucleic acid molecule of the invention operably linked to a heterologous coding sequence, (b) growing the transgenic plant cells comprising the vector, and (c) producing transgenic plants from the transformed plant cells wherein the heterologous coding sequence is specifically expressed in plant roots under control of a nucleic acid molecule of the invention. In one embodiment of this aspect, the transgenic plant is a maize plant or a rice plant. In another embodiment of this aspect, the heterologous coding sequence is selected from the group consisting of insecticidal coding sequences, nematicidal coding sequences, herbicide tolerance coding sequences, anti-microbial coding sequences, anti-fungal coding sequences, anti-viral coding sequences, abiotic stress tolerance coding sequences, nutritional quality coding sequences, visible marker coding sequences and selectable marker coding sequences. In yet another embodiment, the invention provides transgenic plants produced according to this aspect. In a preferred embodiment the transgenic plants are maize plants or rice plants.

In a further aspect, the present invention provides a method of isolating a promoter capable of directing root-specific expression in plants comprising: (a) preparing a nucleic acid probe from any one of SEQ ID NOS: 1-4; (b) hybridizing the nucleic acid probe to either cDNA or genomic DNA prepared from a plant; and (c) isolating a hybridizing sequence from the cDNA or the genomic DNA with at least 70% identity to the nucleic acid probe.

In another aspect, the present invention provides a method of identifying fragments of a promoter capable of directing root-specific expression in plants comprising: (a) providing the isolated promoter sequence according to the invention; (b) generating fragments of the promoter sequence of step (a); (c) transforming plants with the fragments of step (b) operably linked to a heterologous coding sequence; and (d) identifying the fragments of step (b) having promoter activity in a transgenic plant by expression of the heterologous coding sequence.

Also provided by the present invention is a primer comprising at least 16 contiguous nucleotides of any one of SEQ ID NOS: 1-4. Further, the present invention provides a hybridization probe comprising at least 50 contiguous nucleotides of any one of SEQ ID NOS: 1-4.

BRIEF DESCRIPTION OF THE SEQUENCES IN THE SEQUENCE LISTING

SEQ ID NO: 1 is the nucleotide sequence of the MRS1 promoter.

SEQ ID NO: 2 is the nucleotide sequence of the MRS2 promoter.
SEQ ID NO: 3 is the nucleotide sequence of the MRS3 promoter.
SEQ ID NO: 4 is the nucleotide sequence of the MRS4 promoter.
SEQ ID NO: 5 is the sequence of the root-specific cDNA designated 22P8.
SEQ ID NO: 6 is the predicted amino acid sequence encoded by SEQ ID NO: 5.
SEQ ID NO: 7 is the sequence of the root-specific cDNA designated 10B21.
SEQ ID NO: 8 is the predicted amino acid sequence encoded by SEQ ID NO: 7.
SEQ ID NO: 9 is the sequence of the root-specific cDNA designated 2D14.
SEQ ID NO: 10 is the predicted amino acid sequence encoded by SEQ ID NO: 9.
SEQ ID NO: 11 is the sequence of the root-specific cDNA designated 4H19.
SEQ ID NO: 12 is the predicted amino acid sequence encoded by SEQ ID NO: 11.
SEQ ID NOS: 13-16 are primers useful in isolating 22P8 cDNA and related sequences.
SEQ ID NOS: 17-20 are primers useful in isolating 10B21 cDNA and related sequences.
SEQ ID NOS: 21-22 are primers useful in isolating 2D14 cDNA and related sequences.
SEQ ID NOS: 23-26 are primers useful in isolating 4H19 cDNA and related sequences.
SEQ ID NO: 27 is an adapter primer useful according to the present invention.
SEQ ID NO: 28 is a primer useful in isolating the 22P8 promoter and related sequences.
SEQ ID NOS: 29-30 are primers useful in isolating the 10B21 promoter and related sequences.
SEQ ID NOS: 31-32 are primers useful in isolating the 2D14 promoter and related sequences.
SEQ ID NOS: 33-34 are primers useful in isolating the 4H19 promoter and related sequences.
SEQ ID NO: 35 is an adapter primer useful according to the present invention.
SEQ ID NO: 36 is the 22P8GSP7 forward primer.
SEQ ID NO: 37 is a 5'λ arm primer.
SEQ ID NO: 38 is a 3'λ arm primer.
SEQ ID NOS: 39-40 are primers useful in amplifying the MRS1L promoter.
SEQ ID NOS: 41-42 are primers useful in adding att sites to the MRS1L promoter.
SEQ ID NOS: 43-44 are primers useful in adding attB1 and attB2 sites to the 5' and 3' ends of the promoters of the present invention.
SEQ ID NO: 45 is a primer useful in amplifying the MRS1S promoter.
SEQ ID NO: 46 is a primer useful adding att sites to the MRS1S promoter.
SEQ ID NOS: 47-50 are primers useful in amplifying the MRS2 promoter.
SEQ ID NOS: 51-52 are primers useful in adding att sites to the MRS2 promoter.
SEQ ID NOS: 53-54 are primers useful in amplifying the MRS3 promoter.
SEQ ID NOS: 55-56 are primers useful in adding att sites to the MRS3 promoter.
SEQ ID NOS: 57-59 are primers useful in amplifying the MRS4 promoter.

SEQ ID NOS: 60-61 are primers useful in adding att sites to the MRS4 promoter.
SEQ ID NOS: 62-63 are primers useful in constructing a binary destination vector according to the present invention.
SEQ ID NOS: 64-67 are primers useful in isolating the MRS2M and MRS2S promoters.

DEFINITIONS

"Antisense inhibition" refers to the production of antisense RNA transcripts capable of suppressing the expression of protein from an endogenous gene or a transgene.

"Chimeric" is used to indicate that a DNA sequence, such as a vector or a gene, is comprised of two or more DNA sequences of distinct origin that are fused together by recombinant DNA techniques resulting in a DNA sequence, which does not occur naturally.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Constitutive promoter" refers to a promoter that is able to express the gene that it controls in all or nearly all of the plant tissues during all or nearly all developmental-stages of the plant, thereby generating "constitutive expression" of the gene.

"Co-suppression" and "sense suppression" refer to the production of sense RNA transcripts capable of suppressing the expression of identical or substantially identical transgene or endogenous genes (U.S. Pat. No. 5,231,020).

"Contiguous" is used herein to mean nucleic acid sequences that are immediately preceding or following one another.

"Corn rootworm" or "corn rootworms", as used herein, refer to insects of the genus *Diabrotica*, including the southern corn rootworm, the northern corn rootworm, the western corn rootworm, and the Mexican corn rootworm either in the larval or adult stage, preferably in the larval stage. The root-specific promoters of the invention are used to express corn rootworm toxins in the roots of transgenic plants thus protecting fields of transgenic plants from corn rootworm damage. The term "corn rootworm" and *Diabrotica* are herein used interchangeably.

"Expression" refers to the transcription and stable accumulation of mRNA. Expression may also refer to the production of protein.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components.

The "expression pattern" of a promoter (with or without an enhancer) is the pattern of expression level that shows where in the plant and in what developmental stage the promoter initiates transcription. Expression patterns of a set of promoters are said to be complementary when the expression pattern of one promoter shows little overlap with the expression pattern of the other promoter.

"Gene" refers to a nucleic acid fragment that expresses mRNA, functional RNA, or specific protein, including regulatory sequences. The term "Native gene" refers to a gene as found in nature. The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes. (English, et al., 1996, Plant Cell 8:179-1881). Gene silencing includes virus-induced gene silencing (Ruiz et al., 1998, Plant Cell 10:937-946).

"Genetically stable" and "heritable" refer to chromosomally-integrated genetic elements that are stably maintained in the plant and stably inherited by progeny through successive generations.

"Heterologous DNA Sequence" is a DNA sequence not naturally associated with a host cell into which it is introduced, including non-naturally occurring multiple copies of a naturally occurring DNA sequence.

"Inducible promoter" refers to those regulated promoters that can be turned on in one or more cell types by an external stimulus, such as a chemical, light, hormone, stress, or a pathogen.

"Insecticidal" is defined as a toxic biological activity capable of controlling insects, preferably by killing them.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency. (Turner et al., 1995, Molecular Biotechnology, 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989, Plant Cell, 1:671-680).

The term "nucleic acid" refers to a polynucleotide of high molecular weight which can be single-stranded or double-stranded, composed of monomers (nucleotides) containing a sugar, phosphate and a base which is either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably-linked" and "Operatively-linked" refer to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Overexpression" refers to the level of expression in transgenic organisms that exceeds levels of expression in normal or untransformed organisms.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Preferred expression" is the expression of gene products that are preferably expressed at a higher level in one or a few plant tissues (spatial limitation) and/or to one or a few plant developmental stages (temporal limitation) while in other tissues/developmental stages there is a relatively low level of expression.

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The terms "protein," "peptide" and "polypeptide" are used interchangeably herein.

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Promoters may be derived in their entirety from a native gene, or be composed of different elements derived from different promoters found in nature, or even be comprised of synthetic DNA segments. A "minimal or core promoter" is a promoter consisting only of all basal elements needed for transcription initiation, such as a TATA-box and/or initiator.

"Reference sequence" as used herein is defined as a sequence that is used as a basis for sequence comparison. A reference sequence may be a subset or the entirety of a specified sequence; for example, as a fragment of a full-length cDNA or gene sequence, or the full-length cDNA or gene sequence.

"Regulated promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived by posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA. A "functional RNA" refers to an antisense RNA, ribozyme, or other RNA that is not translated. (but participates in a reaction or process as an RNA).

A "selectable marker gene" refers to a gene whose expression in a plant cell gives the cell a selective advantage. The selective advantage possessed by the cells transformed with the selectable marker gene may be due to their ability to grow in presence of a negative selective agent, such as an antibiotic or a herbicide, compared to the ability to grow of non-transformed cells. The selective advantage possessed by the transformed cells may also be due to their enhanced capacity, relative to non-transformed cells, to utilize an added compound as a nutrient, growth factor or energy source. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

"Specific expression" is the expression of gene products that is limited to one or a few plant tissues (spatial limitation) and/or to one or a few plant developmental stages (temporal limitation).

Substantially identical: the phrase "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Those of skill in the art understand that to avoid a high similarity to a reference sequence due to inclusion of gaps in the polynucleotide sequence a gap penalty is typically introduced and is subtracted from the number of matches.

Optimal alignment of sequences for comparison can be conducted, e.g., by the local homology algorithm of Smith & Waterman, 1981, Adv. Appl. Math. 2: 482, by the homology alignment algorithm of Needleman & Wunsch, 1970, J. Mol. Biol. 48: 443, by the search for similarity method of Pearson & Lipman, 1988, Proc. Nat'l. Acad. Sci. 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., 1990, J. Mol. Biol. 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, 1989, Proc. Natl. Acad. Sci. 89: 10915).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Another indication that two nucleic acid sequences are substantially identical is that the two molecules hybridize to each other under stringent hybridization conditions. The phrase "hybridizing specifically to" refers to the binding, duplexing, or hybridizing of a molecule only to a particular nucleotide sequence under stringent hybridization conditions when that sequence is present in a complex mixture (e.g., total cellular) of DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2, "Overview of principles of hybridization and the strategy of nucleic acid probe assays", Elsevier, N.Y. Generally, high stringency hybridization and wash conditions are selected to be about 5° C. lower than the thermal melting point ($T_m$) for the specific sequence at a defined ionic strength and pH. Typically, under high stringency conditions a probe will hybridize to its target subsequence, but to no other sequences.

The $T_m$ is the temperature (under defined ionic strength and pH) at which 50% of the target sequence hybridizes to a perfectly matched probe. Very high stringency conditions are selected to be equal to the $T_m$ for a particular probe. An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, for example, when a copy of a nucleic acid is created using the maximum codon degeneracy permitted by the genetic code.

Low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium. citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 0% formamide, 1 M NaCl, 1% SDS at 37° C., and a wash in 0.1×SSC at 60 to 65° C.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

Specificity is typically the function of post-hybridization washes, the critical factors being the ionic strength and temperature of the final wash solution. For DNA-DNA hybrids, the T$_m$ can be approximated from the equation of Meinkoth and Wahl Anal. Biochem. 138:267-284 (1984); TM 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The TM is the temperature (under defined ionic strength and pH) at which 50% of a complementary target sequence hybridizes to a perfectly matched probe. T is reduced by about 1° C. for each 1% of mismatching; thus, TM, hybridization, and/or wash conditions can be adjusted to hybridize to sequences of the desired identity. For example, if sequences with >90% identity are sought, the T$_m$ can be decreased 10° C. Generally, high stringency conditions are selected to be about 19° C. lower than the thermal melting point (T$_m$) for the specific sequence and its complement at a defined ionic strength and pH. However, very high stringency conditions can utilize a hybridization and/or wash at 1, 2, 3, or 4° C. lower than the thermal melting point (T$_m$); moderately stringent conditions can utilize a hybridization and/or wash at 6, 7, 8, 9, or 10° C. lower than the thermal melting point (T$_m$); low stringency conditions can utilize a hybridization and/or wash at 11, 12, 13, 14, 15, or 20° C. lower than the thermal melting point (T$_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, N.Y.); and Ausubel et al., eds. (1995) Current Protocols in Molecular Biology, Chapter 2 (Greene Publishing and Wiley—Interscience, New York). See Sambrook et al. (1989) Molecular Cloning: A Laboratory Manual (2d ed., Cold Spring Harbor Laboratory Press, Plainview, N.Y.).

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Tissue-specific promoter" refers to regulated promoters that are not expressed in all plant cells but only in one or more cell types in specific organs (such as leaves, roots or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Transactivating gene" refers to a gene encoding a transactivating protein. It can encode a transcription factor. It can be a natural gene, for example, a plant transcriptional activator, or a chimeric gene, for example, when plant regulatory sequences are operably-linked to the open reading frame of a transcription factor from another organism. "Transactivating genes" may be chromosomally integrated or transiently expressed. "Trans-activation" refers to switching on of gene by the expression of another (regulatory) gene in trans.

A "transcriptional cassette" will comprise in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The "transcription initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

The term "transformation" refers to the transfer of a nucleic acid fragment into the genome of a host cell, resulting in genetically stable inheritance. "Transiently transformed" refers to cells in which transgenes and foreign DNA have been introduced (for example, by such methods as *Agrobacterium*-mediated transformation or biolistic bombardment), but not selected for stable maintenance. "Stably transformed" refers to cells that have been selected and regenerated on a selection media following transformation.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"Transient expression" refers to expression in cells in which a virus or a transgene is introduced by viral infection or by such methods as *Agrobacterium*-mediated transformation, electroporation, or biolistic bombardment, but not selected for its stable maintenance.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

"Visible marker" refers to a gene whose expression does not confer an advantage to a transformed cell but can be made detectable or visible. Examples of visible markers include but are not limited to β-glucuronidase (GUS), luciferase (LUC) and green fluorescent protein (GFP).

"Wild-type" refers to the normal gene, virus, or organism found in nature without any known mutation.

DETAILED DESCRIPTION OF THE INVENTION

Identification of Root-Specific Genes, Promoters and Homologues

In many instances, it is desirable to spatially regulate the expression of a transgene so as to be expressed only in plant root tissues. A promoter capable of directing expression in a specific or preferential manner can most expeditiously accomplish this spatial regulation.

The present invention provides isolated nucleic acid molecules having a nucleotide sequence that directs root-specific transcription in a plant. Root-specific promoters are isolated by identifying genes that are specifically expressed in root tissue of a target plant and subsequently isolating the regulatory sequences of these genes. In one method as further described in the examples below, a PCR-subtractive approach is used. Messenger RNA (mRNA) is isolated from maize root-tissue as well as from a combination of non-root tissues from maize, such as leaf, stem, and reproductive tissues. Complimentary DNA (cDNA) is made from each mRNA population and subsequently each cDNA population is digested with a restriction enzyme. Adapter primers, short DNA sequences, are ligated to the 5' and 3' ends of root-specific cDNA. The root-specific and non-root cDNA fragment populations are then hybridized and PCR is used to selectively amplify root-specific cDNA fragments which are not present in the non-root cDNA population and thus do not hybridize with the non-root cDNA fragment population. The amplified cDNA fragments represent fragments of root-specific genes. Using this method root-specific fragments are obtained. Longer sequences, full-length or near full-length cDNA clones of these genes can be obtained by PCR techniques or hybridization. Using a technique known in the art as RACE (rapid amplification of cDNA ends), gene-specific primers are made to the 5' region of the known sequence of each root-specific fragment and PCR is performed on a root-specific cDNA library in which the 5' end of each cDNA of the library has been ligated to a short nucleotide adapter sequence. PCR is used to amplify the region between the gene-specific primer and the adapter sequence. Root-specific cDNA clones exemplified herein by SEQ ID NOS: 5, 7, 9, and 11, were obtained generally using this technique.

Promoter sequences are obtained by cloning the genomic sequences that are homologous to the root-specific cDNA sequences. Genomic sequences may be obtained by hybridization methods or by using PCR methods to extend the sequence in either the 5' or 3' direction from the known sequence (sometimes referred to as "genome walking"). For example, to obtain genomic sequences 5' to the known sequence of the cDNA, primers are made to the sequence near the 5' end of the cDNA. A genomic library is constructed with the 5' end of each genomic DNA sequence ligated to a short oligonucleotide adapter. PCR with a primer hybridizing to the adapter sequence and a 5' primer of a root-specific cDNA sequence allows amplification of a genomic sequence residing 5' to the homologous sequence of the root-specific sequence. DNA sequences obtained from genome walking are sequenced and if additional 5' regions are desired, the process is repeated with primers now at the 5' end of the longest obtained clone. Genomic sequences homologous to root-specific cDNA sequences are also obtained by hybridization under high stringency conditions. High stringency conditions select for hybridization of a probe made from a root-specific cDNA sequence to hybridize to its homologous sequence in the genomic DNA. The genomic DNA is comprised in a genomic DNA library of 5-20 kb maize genomic DNA sequences in a lambda phage vector. Genomic clones that hybridize with the root-specific cDNA are isolated and sequenced.

The genomic clones may include intron sequences, not found in the mRNA or the cDNA clones. The genomic sequences may additionally comprise 5' untranslated sequences, 3' untranslated sequences, and 5' and 3' regulatory sequences. Promoter sequences are found within the genomic sequence 5' to the cDNA sequence. Genomic sequences are cloned which are homologous to the root-specific cDNA sequences. Sequences that are 5' to the sequence homologous to the cDNA sequence are herein referred to as the 5' flanking region which comprises the promoter region.

Promoter and other regulatory sequences are mapped by comparison of the genomic sequence with the homologous root-specific cDNA sequences as well as using sequence homology comparisons to locate the TATA box and other regulatory elements such as binding sites for known plant transcription factors (Guifoyle, T J, 1997, Genetic Engineering 19: 15-47; Meisel and Lam, 1997, Genetic Engineering 19: 183-199). Promoters exemplified herein are set forth in SEQ ID NOS: 1-4.

In one embodiment of the invention, to further delineate the sequences required for root-expression as well as those regulatory sequences that influence the overall level of expression, deletions of the root-specific promoter regions are made. Deletions are made in the 5' flanking region of each root-specific clone. In most promoters 500-1000 base pairs (bp) of 5' flanking sequence are sufficient for promoter activity, including tissue-specific activity. Deletions of the 5' flanking region can result in promoter regions of approximately 50 bp, 100 bp, 250 bp, 500 bp, 750 bp and 1000 bp or more. These promoter deletion sequences serve a two-fold purpose. The deletions allow the further mapping of regulatory sequences within the 5' flanking sequence of each root-specific genomic clone. Additionally, the deletions provide a toolbox of promoter and regulatory sequences that vary in their expression levels and expression patterns thus providing additional flexibility in choosing promoter sequences for appropriate gene regulation. Exemplified herein are fully functional shorter fragments of a promoter designated MRS1 (SEQ ID NO: 1) and a promoter designated MRS2 (SEQ ID NO: 2). The fully functional shorter fragment of MRS1 comprises nucleotides 603-1392 of SEQ ID NO: 1 and is designated MRS1S. One fully functional shorter fragment of MRS2 comprises nucleotides 921-2869 of SEQ ID NO: 2 and is designated MRS2-M. Another fully functional shorter fragment of MRS2 comprises nucleotides 1913-2869 of SEQ ID NO: 2 and is designated MRS2-S.

It is also clear to one skilled in the art that mutations, insertions, deletions and/or substitutions of one or more nucleotides can be introduced into the nucleotide sequences of SEQ ID NOS: 1-4 using methods known in the art. In addition, shuffling the sequences of the invention can provide new and varied nucleotide sequences.

To test for a function of variant DNA sequences according to the invention, such as deletion fragments of SEQ ID NOS: 1-4, the sequence of interest is operably linked to a selectable or visible marker gene and expression of the marker gene is tested in transient expression assays with isolated root tissue or cells or by stable transformation into plants. It is known to the skilled artisan that DNA sequences capable of driving expression of an associated coding sequence are built in a modular way. Accordingly, expression levels from shorter DNA fragments may be different than the one from the longest fragment and may be different from each other. For example, deletion of a down-regulating upstream element will lead to an increase in the expression levels of the associated coding sequence while deletion of an up-regulating element will decrease the expression levels of the associated coding sequence. It is also known to the skilled artisan that deletion of development-specific or a tissue-specific elements will lead to a temporally or spatially altered expression profile of the associated coding sequence.

In another embodiment of the invention, DNA and genomic DNA sequences homologous to SEQ ID NOS: 1-4 or SEQ ID NOS: 5, 7, 9, and 11 may be isolated from other maize germplasm using either hybridization or PCR techniques well known in the art. The isolated sequences may be identical to SEQ ID NOS: 1-4 or SEQ ID NOS: 5, 7, 9, and 11 or they may be substantially identical to SEQ ID NOS: 1-4 or SEQ ID NOS: 5, 7, 9, and 11. It is not necessary for the sequences obtained from other maize germplasm to contain identical nucleotide sequences to be functionally identical to the sequences disclosed herein. Some nucleotide deletions, additions, and replacements may have no impact or only a minor impact on gene expression. A preferable isolated nucleic acid molecule, according to the present invention, comprises a nucleotide sequence that has at least 70% identity to any one of the nucleotide sequences set forth in SEQ ID NOS: 1-4. A more preferable isolated nucleic acid molecule comprises a nucleotide sequence that has at least 80% identity to any one of the nucleotide sequences set forth in SEQ ID NOS: 1-4. An even more preferable isolated nucleic acid molecule comprises a nucleotide sequence that has at least 90% identity to any one of the nucleotide sequences set forth in SEQ ID NOS: 1-4. An even more preferable isolated nucleic acid molecule comprises a nucleotide sequence that has at least 95% identity to any one of the nucleotide sequences set forth in SEQ ID NOS: 1-4. An even more preferable isolated nucleic acid molecule comprises a nucleotide sequence that has at least 99% identity to any one of the nucleotide sequences set forth in SEQ ID NOS: 1-4. The most preferable isolated nucleic acid molecule comprises any one of the nucleotide sequences set forth is SEQ ID NOS: 1-4.

In another embodiment of the invention, cDNA and genomic DNA sequences may be cloned from other plants that represent homologues of the root-specific maize genes and promoters. These homologues allow one to obtain additional root-specific promoters useful for the regulation of multiple genes in the root. Hybridization using the maize cDNA and genomic sequences or portions thereof is used to screen for homologous or substantially identical sequences in other plant genomes. These sequences may comprise only a subset of the nucleotides of SEQ ID NOS: 1-4. A preferable length of homology is 20 base pairs (bp) in length, more preferably, 50 bp in length, and most preferably at least 100 bp in length. In one embodiment of the present invention, a hybridization probe is prepared from any one SEQ ID NOS: 1-4 or portions thereof or SEQ ID NOS: 5, 7, 9, or 11 or portions thereof. Hybridization of such sequences may be carried out under high stringency conditions. Alternatively, low or moderate stringency conditions can be used to allow some mismatching in sequences so that lower degrees of similarity are detected (heterologous probing). Generally, a probe is less than about 1000 nucleotides in length, preferably less than 500 nucleotides in length.

In another embodiment of the present invention, cDNA and genomic sequences are isolated by preparing primers comprising sequences within any one of SEQ ID NOS: 1-4 or comprising primer sequences from SEQ ID NOS: 5, 7, 9, or 11. The primers may be used in a PCR reaction with cDNA or genomic DNA from a plant to obtain homologous sequences or sequences with substantial identity to any one of SEQ ID NOS: 1-4.

Construction of Expression Cassettes

Expression cassettes are constructed comprising the 5' flanking sequences of the root-specific genomic clones. In one embodiment of the present invention, the promoter region utilized in each expression cassette comprises the 5' flanking region up to and including the start of translation. The start of translation is denoted by the first ATG of the open reading frame (ORF) found in the cDNA and the homologous genomic sequence. Thus, the promoter region may include 5' untranslated leader sequence as well as the transcriptional start site, core promoter and additional regulatory elements. In another embodiment of the present invention, expression cassettes are constructed comprising the 5' flanking sequence of the root-specific genomic clones up to and including the transcriptional initiation site. The transcriptional initiation site may be defined by the first nucleotide of the longest cDNA clone obtained. Additionally, the transcriptional initiation site may be further defined by use of techniques well known in the art including RACE PCR, RNase protection mapping and primer extension analysis.

The expression cassettes may further comprise a transcriptional terminator, downstream (3') to the promoter. A variety of transcriptional terminators are available for use in expression cassettes. The transcriptional terminator is responsible for the termination of transcription beyond the transgene and correct mRNA polyadenylation of the mRNA transcript. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used. For example, the 3' flanking sequence comprising genomic sequence 3' to the region homologous to a root-specific cDNA clone may be used.

In a preferred embodiment of the present invention a heterologous coding sequence, for example, an insecticidal coding sequence, a visible marker coding sequence, or a selectable marker coding sequence, is cloned between a promoter of the invention and transcriptional terminator whereby the heterologous coding sequence is operatively linked to the promoter and the transcriptional terminator is operatively linked to the heterologous coding sequence. Examples of visible markers useful for the present invention include, but are not limited to, β-glucuronidase (GUS), Chloramphenicol Acetyl Transferase (CAT), Luciferase (LUC) and proteins with fluorescent properties, such as Green Fluorescent Protein (GFP) from *Aequora victoria*. In principle, many more proteins are suitable for this purpose, provided the protein does not interfere with essential plant functions. Further examples of heterologous coding sequences useful for the present invention include, but are not limited to, antibiotic resistance, virus resistance, insect resistance, disease resistance, or resistance to other pests, herbicide tolerance, improved nutritional value, improved performance in an industrial process or altered reproductive capability. In a preferred embodiment of the present invention, a gene encoding for resistance to insects that feed on the roots of the plant is cloned between the promoter and terminator. In another embodiment of the present invention a sequence encoding a functional RNA such as antisense RNA, a sense RNA for sense-suppression, or a double stranded RNA may also be cloned between the promoter and transcriptional terminator.

Numerous sequences have been found to enhance gene expression from within the transcriptional unit and these sequences can be used in conjunction with the promoters of this invention to increase their expression in transgenic plants. Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183-1200 (1987)). In the same experimental system, the intron from the maize bronze1 gene had a similar effect in enhancing expression. Intron sequences have been routinely incorporated into plant transformation vectors, typically within the non-translated leader. A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693-8711 (1987); Skuzeski et al. *Plant Molec. Biol.* 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126-6130 (1989)); potyvirus leaders, for example, TEV leader (Tobacco Etch Virus) (Allison et al., 1986); MDMV leader (Maize Dwarf Mosaic Virus); *Virology* 154:9-20); human immunoglobulin heavy-chain binding protein (BiP) leader, (Macejak, D. G., and Sarnow, P., *Nature* 353: 90-94 (1991); untranslated leader from the coat protein mRNA of alfalfa mosaic virus (AMV RNA 4), (Jobling, S. A., and Gehrke, L., *Nature* 325:622-625 (1987); tobacco mosaic virus leader (TMV), (Gallie, D. R. et al., *Molecular Biology of RNA*, pages 237-256 (1989); and Maize Chlorotic Mottle Virus leader (MCMV) (Lommel, S. A. et al., *Virology* 81:382-385 (1991). See also, Della-Cioppa et al., *Plant Physiology* 84:965-968 (1987).

Plant Transformation Methods Useful for the Invention

Numerous transformation vectors available for plant transformation are known to those of ordinary skill in the plant transformation art, and the nucleic acid molecules of the invention can be used in conjunction with any such vectors. The selection of vector will depend upon the preferred transformation technique and the target plant species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet 79: 625-631 (1990)), the hph gene, which confers resistance to the antibiotic hygromycin (Blochinger & Diggelmann, Mol Cell Biol 4: 2929-2931), and the Aft gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446-455 (1985)) allowing excision of the tetracycline-resistance gene, followed by insertion of an AccI fragment from pUC4K carrying an NPTII (Messing & Vierra, Gene 19: 259-268 (1982): Bevan et al., Nature 304: 184-187 (1983): McBride et al., Plant Molecular Biology 14: 266-276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153-161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

pCIB10 And Hygromycin Selection Derivatives Thereof:

The binary vector pCIB10 (Rothstein et al. (Gene 53: 153-161 (1987)) contains a gene encoding kanamycin resistance for selection in plants and T-DNA right and left border sequences and incorporates sequences from the wide host-range plasmid pRK252 allowing it to replicate in both *E. coli* and *Agrobacterium*. Various derivatives of pCIB10 that incorporate the gene for hygromycin B phosphotransferase are described by Gritz et al. (Gene 25: 179-188 (1983)). These derivatives enable selection of transgenic plant cells on hygromycin only (pCIB743), or hygromycin and kanamycin (pCIB715, pCIB717).

Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

pCIB3064:

pCIB3064 is a pUC-derived vector suitable for direct gene transfer techniques in combination with selection by the herbicide Basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 bp digestion with SalI and SacI; the termini rendered blunt and re-ligated to generate plasmid pCIB3060. The plasmid pJIT82 is obtained from the John Innes Centre, Norwich and the 400 bp SmaI fragment containing the bar gene from *Streptomyces viridochromogenes* is excised and inserted into the HpaI site of pCIB3060 (Thompson et al. EMBO J 6: 2519-2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 that contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

Transformation Methods Useful for the Present Invention

Once a nucleic acid molecule of the invention has been cloned into an expression cassette, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis thaliana*, and woody plants such as coniferous and deciduous trees, especially maize, wheat, or sugar beet.

Once an expression cassette is transformed into a particular plant species, the expression cassette may be propagated in that species or moved into other varieties of the same species, particularly including commercial varieties, using traditional breeding techniques.

Transformation of Dicotyledons

Transformation techniques for dicotyledons are well known in the art and include both *Agrobacterium*-based and non *Agrobacterium* based techniques. Non-*Agrobacterium* techniques involve the uptake of exogenous genetic material directly by protoplasts or cells. This can be accomplished by particle bombardment-mediated delivery, microinjection, or PEG or electroporation mediated uptake. Examples of these techniques are described by Paszkowski et al., EMBO J 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a tri-parental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the vector can surround the target cell so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, embryos that are 0.75-1 mm in length are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described in WO 94/00977 and U.S. Pat. No. 5,591,616, both of which are incorporated herein by reference. A preferred method of maize transformation is described in Negrotto et al., (Plant Cell Reports 19: 798-803 (2000)), incorporated herein by reference.

Analysis of Promoter Activity

Several methods are available to assess promoter activity. Expression cassettes are constructed with a visible marker, as described above. Transient transformation methods are used to assess promoter activity. Using transformation methods such as microprojectile bombardment, *Agrobacterium* transformation or protoplast transformation, expression cassettes are delivered to plant cells or tissues. Reporter gene activity, such as β-glucuronidase activity, luciferase activity or GFP fluorescence is monitored after transformation over time, for example 2 hours, 5 hours, 8 hours, 16 hours, 24 hours, 36 hours, 48 hours and 72 hours after DNA delivery using methods well known in the art. Reporter gene activity may be monitored by enzymatic activity, by staining cells or tissue with substrate for the enzyme encoded by the reporter gene or by direct visualization under an appropriate wavelength of light. Full-length promoter sequences, deletions and mutations of the promoter sequence may be assayed and their expression levels compared. Additionally, RNA levels may be measured using methods well known in the art such as Northern blotting, competitive reverse transcriptase PCR and RNAse protection assays. These assays measure the level of expression of a promoter by measuring the 'steady state' concentration of a standard transcribed reporter mRNA. This measurement is indirect since the concentration of the reporter mRNA is dependent not only on its synthesis rate, but also on the rate with which the mRNA is degraded. Therefore the steady state level is the product of synthesis rates and degradation rates. The rate of degradation can however be considered to proceed at a fixed rate when the transcribed sequences are identical, and thus this value can serve as a measure of synthesis rates.

Further confirmation of promoter activity is obtained by stable transformation of the promoter in an expression cassette comprising a visible marker or gene of interest into a plant as described above. Using the various methods described above such as enzymatic activity assays, RNA analysis and protein assays as described supra, promoter activity is monitored over development, and additionally by monitoring expression in different tissues in the primary transformants and through subsequent generations of transgenic plants.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual*, 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Construction of Maize Root Forward and Reverse Subtracted cDNA Libraries

As a first step towards the identification of maize root-specific cDNA clones, subtracted cDNA libraries were constructed using Clontech's PCR-Select cDNA Subtraction Kit (Clontech Cat. No. K1804-1). Two different subtracted cDNA libraries were constructed; 1) a forward-subtracted library enriched for differentially expressed transcripts that are specific to the root, and 2) a reverse-subtracted library enriched for differentially expressed transcripts that are specific to all aboveground tissues exclusive of roots. Total RNA was isolated from maize line CG00526 including tassel, silks, seed, stem, leaf, and roots using tissue samples pooled from mature and several developmental stages for each organ. For the root, crown roots, primary roots and lateral roots were sampled from approximately five evenly divided developmental stages starting two weeks post germination and ending at maturity. Poly A mRNA was isolated from each of the total RNA preps using procedures outlined in the PolyATtract mRNA isolation Systems kit (Promega Cat. No. Z3790). cDNAs were synthesized from polyA mRNA from each organ, digested with Rsa I, ligated to adaptors, and divided into "tester cDNA", and "driver cDNA" populations. For the forward-subtracted library the "tester cDNA" was represented by the root cDNA and the "driver cDNA" was composed of equal quantities of tassel, silk, seed, stem, and leaf cDNAs. For the reverse-subtracted library the "tester" and "driver" cDNA populations were the reverse of those used in the forward-subtracted library.

The cDNA subtraction and PCR amplification for each of the libraries was carried out as described in the user's manual of the Clontech PCR-Select cDNA Subtraction Kit. The PCR products of the root-specific forward-subtracted library were cloned into both the TA-cloning vector pCR2.1 (Invitrogen Cat. No. K20000-01) and into pBSK$^-$ (Stratagene Cat. No. 212206). cDNAs ligated into pBSK$^-$ were transformed into E. coli strain DH10B cells (Life Technologies Cat. No. 18290-015) by electroporation. Transformation reactions were plated onto Q-trays (Genetix) containing media enabling blue/white colony selection. White colonies on Q-trays were robotically picked (Q-bot) into 384-well plates containing antibiotic selection media and cryoprotectant. Colonies in 384-well plates were grown up and frozen-off at −80° C. Approximately 16,000 colonies were picked. Each of the approximately 16,000 gridded bacterial colonies representing the maize root subtracted library was robotically arrayed as duplicate spots on replicate 23 cm$^2$ nylon membranes using a Q-bot (Genetix Limited). Colonies were grown up on membranes overlaid onto selective agar trays and subsequent in situ bacterial colony lysis and processing of membrane for hybridization were performed according to Nizetic et al. (Nucleic Acids Res. 19(1): 182, (1991)).

Example 2

Screening of Maize Root Subtracted cDNA Library, Sequencing of Clones and Confirmation of Root Specificity by Northern Blot Analysis Differential hybridization screening of the arrayed library with $^{32}$P-labeled probes were performed in order to identify clones whose expression was specific to the root. This was accomplished by hybridizing one of the two replicate arrays of the library with a forward-subtracted probe made from the same subtracted cDNA that was used to construct the forward-subtracted library; and hybridizing the second replica array with a reverse-subtracted probe using the same subtracted cDNA used to construct the reverse-subtracted library. Probe production and hybridizations were performed according to the users manual of the PCR-Select Differential Screening Kit (Clontech Cat. No. K1808-1, -D). Nylon membranes were exposed to both film (Kodak Biomax) and phosphoimager screens and densitometry values were assigned to each of the spots.

Using visual inspection of autoradiographs and densitometry data, 300 clones were picked for sequencing. Clones were picked on their ability to satisfy three criteria; 1) No hybridization to the reverse-subtracted probe, 2) Strong hybridization to the forward-subtracted probe, and 3) Consistent hybridization intensity between duplicate spots on the same filter. The 300 sequences were arranged into 70 unique contigs using the Phred/Phrap program (Codon Code Corp.) for sequence analysis and contig assembly. Sequence identities were searched using the Blast program and clones giving the same blast ID were eliminated. The resulting 36 unique clones were then evaluated for root-specific expression by northern blot analysis.

Gel blots containing 18 μg of total RNA (isolated from tissues at several developmental stages for each sample) from each of six different organs, tassel, silk, seed, leaf, stem, and root were hybridized with $^{32}$P-labeled probes made from each of the 36 cDNAs. These analyses confirmed that 15 clones (2A12, 10B21, 4J8, 16M14, 29D21, 7B21, 14116, 2D14, 16H17, 36E7, 4H19, 2P9, 6G15, 22P8, and SM13) had root-specific expression.

The 15 cDNA clones from above were then subjected to reverse northern blot analysis to evaluate whether any of the previously observed root-specific expression might be due to expression that is confined to or predominant in the root tip. Five duplicate gel blots of the 15 root-specific cDNA clones were prepared and each was hybridized with a first-strand $^{32}$P-labeled cDNA probe prepared from polyA$^+$ RNA isolated from either whole roots, root-tips, roots without tips, crown root tips, or crown roots without tips. The intensity of the $^{32}$P-labeled band on the autoradiograph was characterized as high (+++), medium (++), low (+), or absent (−). The results shown in Table 1 indicate that expression of all 15 clones was not confined to the root tip and that substantial expression was found throughout the root.

TABLE 1

Results of Northern and Reverse Northern Analysis.

| Clone | Relative Levels of mRNA in Northern | Relative Levels of mRNA in Reverse Northern | | | | |
|---|---|---|---|---|---|---|
| | | Whole roots | Root tips | Roots w/o root tips | Crown root tips | Crown roots w/o root tips |
| 2A12 | +++ | + | + | + | − | + |
| 2D14 | ++ | + | +++ | ++ | +++ | +++ |
| 2P9 | ++ | + | + | + | − | + |
| 4H19 | +++ | +++ | + | +++ | − | ++ |
| 4J8 | +++ | + | + | + | + | + |
| 6G15 | ++ | + | + | + | + | + |
| 7B12 | +++ | +++ | + | +++ | − | ++ |
| 10B21 | ++ | ++ | +++ | ++ | +++ | +++ |
| 14H6 | ++ | + | + | + | + | + |
| 16H17 | +++ | +++ | + | +++ | + | +++ |
| 16M14 | + | +++ | +++ | +++ | ++ | ++ |
| 22P8 | +++ | +++ | ++ | +++ | − | +++ |
| 29D21 | + | ++ | − | + | − | |
| 36E7 | +++ | +++ | + | +++ | − | +++ |
| SM13 | +++ | +++ | +++ | +++ | ++ | − |

Example 3

Obtaining Full-Length cDNA Clones for Selected Root-Specific cDNAs

Using the above northern and reverse northern expression data, four clones, 22P8, 10B21, 2D14, 4H19 were chosen to obtain full-length cDNAs. All four of the original cDNAs for these clones represent 3' fragments each containing poly A tails. 5' RACE PCR using Clontech's Marathon cDNA Amplification Kit (Cat. No. K1802-1) was used to extend the partial cDNA clones. Because of the high G+C content of maize DNA, incremental RACE extensions utilizing the following RACE gene-specific primers (SEQ ID NOS: 13-26) and the adapter primer (SEQ ID NO: 27) were used to obtain the full-length cDNA products:

Gene Specific Primers Used for Each Designated Clone

| Clone | Primer Sequence | SEQ ID NO |
|---|---|---|
| 22P8 | 5'-CACACTAGCGCACAGAGATCAGAG-3' | (SEQ ID NO: 13) |
| | 5'-GCACCAACACAAGCACAACAGAAC-3' | (SEQ ID NO: 14) |
| | 5'-CAGGGTACATCTTGCCGCACTTGC-3' | (SEQ ID NO: 15) |
| | 5'-TGATCCGCAGTTGCAGCTTGATCC-3' | (SEQ ID NO: 16) |
| 10B21 | 5'-CATGCTCGCGGCTAGCTTAGAGG-3' | (SEQ ID NO: 17) |
| | 5'-ACAGTCTTGCCGCAGTGGTTGAG-3' | (SEQ ID NO: 18) |
| | 5'-TGAGGCTGAGGTCGACGGGCAGG-3' | (SEQ ID NO: 19) |
| | 5'-CGAGGTCGACGAGTCCCTTCAGC-3' | (SEQ ID NO: 20) |
| 2D14 | 5'-TTAGCACCGGCGTAGAAGTGATCG-3' | (SEQ ID NO: 21) |
| | 5'-GCATGGAATGGAAGGGAGGCAGC-3' | (SEQ ID NO: 22) |
| 4H19 | 5'-ATACAACGCAAGGTTCGCTCACTG-3' | (SEQ ID NO: 23) |
| | 5'-CATGACCGCTAAGGATCAGGAGAC-3' | (SEQ ID NO: 24) |
| | 5'-TCTTCTTGTGCACCGCCGAAGC-3' | (SEQ ID NO: 25) |
| | 5'-TGCACTCACACCGCCGATGATGG-3' | (SEQ ID NO: 26) |
| Adaptor | 5'-CCATCCTAATACGACTCACTATAGGGC-3' | (SEQ ID NO: 27) |

The results of the RACE extensions of the cDNA clones and the primers utilized for this process are shown in Table 2. A full-length cDNA candidate (SEQ ID Nos: 5, 7, 9, and 11) was obtained for each of the four clones. The full-length or near full-length cDNA clone obtained by RACE PCR allowed for the prediction of the translation initiating ATG for each of the cDNA clones.

TABLE 2

Results of cDNA RACE Extension.

| Clone | Original cDNA size (bp) | Predicted size of full-length cDNA (bp) | 5' RACE primer name | cDNA size obtained by RACE (bp) | cDNA obtained by RACE |
|---|---|---|---|---|---|
| 22P8 | 345 | 650-700 | SEQ ID NO: 13<br>SEQ ID NO: 14<br>SEQ ID NO: 15<br>SEQ ID NO: 16 | 700 | SEQ ID NO: 5 |
| 10B21 | 406 | 700-800 | SEQ ID NO: 17<br>SEQ ID NO: 18<br>SEQ ID NO: 19<br>SEQ ID NO: 20 | 766 | SEQ ID NO: 7 |
| 2D14 | 306 | 700-800 | SEQ ID NO: 21<br>SEQ ID NO: 22 | 730 | SEQ ID NO: 9 |
| 4H19 | 311 | 700-850 | SEQ ID NO: 23<br>SEQ ID NO: 24<br>SEQ ID NO: 25<br>SEQ ID NO: 26 | 660 | SEQ ID NO: 11 |

Example 4

Isolation of Promoter/Genomic Clones Corresponding to the Root-Specific cDNAs

Promoter/genomic clones corresponding to cDNAs 22P8, 10B21, 2D14, 4H19 (SEQ ID NOS: 5, 7, 9, and 11, respectively) were isolated via PCR utilizing either maize "Genome Walker" or λ EMBL3 genomic libraries as template. "Genome walker" adaptor-ligated maize genomic libraries were constructed using DNA from maize line CGC000526 and Clontech's Universal Genome Walker kit (Clontech Cat. No. K1807-1). Five different libraries were constructed, each comprised of genomic DNA fragments generated by digestion with one of the following blunt end restriction enzymes: DraI, EcoRV, HincII, SspI, or StuI. Genome Walker libraries were screened utilizing the following gene-specific primers (SEQ ID NOS: 28-34) and the adapter primer (SEQ ID NO: 35) which was supplied in the kit:

Gene Specific Primers Used for Each Designated Clone

| Clone | Primer Sequence | SEQ ID NO. |
|---|---|---|
| 22P8 | 5'-TCCTCGAGCTCTTTCGTTTGCTTTGGAAAC-3' | (SEQ ID NO: 28) |
| 10B21 | 5'-ACACCACCAGGTTCACGGCGAGGAACAG-3' | (SEQ ID NO: 29) |
| | 5'-GAGGCCTTGCCTGCCATTGCTGCAGAGT-3' | (SEQ ID NO: 30) |

| Clone | Primer Sequence | SEQ ID NO. |
|---|---|---|
| 2D14 | 5'-AGCAGTTGGACGTGCAGGCGTTGGCTAC-3'<br>5'-AGGTTCACGGCCAGGAACAGCGCGAAT-3' | (SEQ ID NO: 31)<br>(SEQ ID NO: 32) |
| 4H19 | 5'-TCTTTCTTGTGCACCGCCGAAGC-3'<br>5'-TGCACTCACACCGCCGATGATGG-3' | (SEQ ID NO: 33)<br>(SEQ ID NO: 34) |
| Adaptor | 5'-GTAATACGACTCACTATAGGGC-3' | (SEQ ID NO: 35) |

PCR conditions were those suggested in the Clontech users manual. PCR reactions were fractionated on agarose gels, and the resulting product band was excised, cloned in a Topo vector and sequenced to verify the correct product. Promoter clones corresponding to cDNAs 22P8, 10B21, 2D14, 4H19 (SEQ ID NOS: 5, 7, 9, and 11, respectively) were cloned from these libraries.

The λ EMBL3 library was custom made by Clontech (Clontech Cat. No. cs1012j) using genomic DNA from maize line CG000526. The 1.4 kb promoter clone corresponding to cDNA 22P8 (SEQ ID NO: 5) was cloned from this library. The library was PCR screened using 22P8GSP7,

5'-ACTATAGGGCACGCGTGGT-3'   (SEQ ID NO: 36)

in conjunction with the following 5' and 3'λ arm primers supplied by Clontech (Cat. No. 9104-1):

(SEQ ID NO: 37)
5'-CTGCTTCTCATAGAGTCTTGCAGACAAACTGCGCAAC-3'

(SEQ ID NO: 38)
5'-TGAACACTCGTCCGAGAATAACGAGTGGATCTGGGTC-3'

PCR was done using conditions suggested in the user manual supplied with the primers. The 22P8 promoter clone was a product of the 3'λ primer and 22P8GSP7 primer.

Example 5

Construction of Root-specific Expression Cassettes

Entry Vectors

The first step in construction of expression cassettes was the cloning of the promoters into an entry vector. PCR primers were designed to amplify each promoter and to place attB1 and attB2 sites on the 5' and 3' ends, respectively. The promoter corresponding to the cDNA 22P8 was designated as Maize Root-Specific 1 or MRS1. Two different promoter constructs were made from MRS1; the full-length MRS1 comprising nucleotides 1 to 1391 of SEQ ID NO: 1, designated MRS1L, and a second shorter fragment of MRS1 comprising nucleotides 601 to 1391 of SEQ ID NO: 1, designated MRS1S. MRS1L was PCR amplified out of Genome Walker library EcoRV with primers 22P8DS1 5'-TTAAGAACATGACGGATGAAGAATCACT-3' (SEQ ID NO: 39) and 22P8GSP6 5'-TGATCCGCAGTTGCAGCTTGATCC-3' (SEQ ID NO: 40) followed by 22P8DS1 (SEQ ID NO: 39) and the nested primer 22P8GSP7 (SEQ ID NO: 36). Att sites were added to MRS1L by PCR amplifying the product of the nested reaction with primers consisting of ½ att and ½ gene-specific sequence, 22P8DS5 5'-ACAAAAAAGCAGGCTGGAACATGACGGATGA-3' (SEQ ID NO: 41) and 22P8DS9 5'-ACAAGAAAGCTGGGTCCTCGAGCTCTTTCG-3' (SEQ ID NO: 42). The full attB1 and attB2 sites were added by using primer attB1 5'-GGGGACAAGTTTGTACAAAAAAGCAGGCT-3' (SEQ ID NO: 43) and attB2 5'-GGGGACCACTTTGTACAAGAAAGCTGGGT-3' (SEQ ID NO: 44). MRS1S (nucleotides 601-1391 of SEQ ID NO: 1) was PCR amplified out of Genome Walker library EcoRV with primers 22P8DS1 (SEQ ID NO: 39) and 22P8GSP6 (SEQ ID NO: 40) followed by the nested primers 22P8DS3 5'-GCGTAGTTGAAGCTTACAAAGTTGCAT-3' (SEQ ID NO: 45) and 22P8GSP7 (SEQ ID NO: 36). Att sites were added to MRS1S by PCR amplifying the product of the nested reaction with primers consisting of ½ att and ½ gene-specific sequence, 22P8DS7 5'-ACAAAAAAGCAGGCTGTAGTTGAAGCTTAC-3' (SEQ ID NO: 46) and 22P8DS9 (SEQ ID NO: 42). The full attB1 and attB2 sites were added by using primers attB1 (SEQ ID NO: 43) and attB2 (SEQ ID NO: 44).

The promoter corresponding to the cDNA 10B21 was designated as MRS2L (SEQ ID NO: 2). MRS2L was amplified out of Genome Walker library EcoRV by PCR amplification with primers 10B21DS1,5'-GACGGCCCGGGCTGGTAAATTGACTT-3' (SEQ ID NO: 47) and 10B21GSP1, 5'-CATGCTCGCGGCTAGCTTAGAGG-3' (SEQ ID NO: 48) followed by the nested primers 10B21DS3,5'-TGGTAAATTGACTTTGCCTAGTGTTGGA-3' (SEQ ID NO: 49) and 10B21GSP2,5'-ACAGTCTTGCCGCAGTGGTTGAG-3' (SEQ ID NO: 50). Att sites were added to MRS2 by PCR amplifying the product of the nested reaction with primers consisting of ½ att and ½ gene-specific sequence, 10B21DS5,5'-ACAAAAAAGCAGGCTTGACTTTGCCTAGTG-3' (SEQ ID NO: 51) and 10B21DS7,5'-ACAAGAAAGCTGGGTTGCTGCAGAGTACAG-3' (SEQ ID NO: 52). The full attB1 and attB2 sites were added by using primers attB1 (SEQ ID NO: 43) and attB2 (SEQ ID NO: 44). Two shorter fragments of MRS2L were made. One fragment of MRS2L comprising nucleotides 921 to 2869 of SEQ ID NO: 2, designated MRS2M, and a second fragment of MRS2L comprising nucleotides 1913 to 2869 of SEQ ID NO: 2, designated MRS2S. Fragments of the MRS2L promoter were generated with PCR using the MRS2L promoter (SEQ ID NO: 2) as template and gene specific primers (SEQ ID NOS: 64-67). The sequence CACC was added to the 5' end of each forward primer to allow directional cloning into the pENTR-D/TOPO plasmid (Invitrogen). This directional cloning produced an entry vector comprising either the MRS2M fragment or the MRS2S fragment. MRS2-specific primers used to make the MRS2 promoter fragments were as follows:

| Primer | Primer Sequence | SEQ ID NO |
|---|---|---|
| MRS2 Rev | 5'-GCTGCAGAGTACAGAAAGCA-3' | SEQ ID NO: 64 |
| MRS2L Fwd | 5'-CACCGGCTTGACTTTGCCTAGTGT-3' | SEQ ID NO: 65 |
| MRS2M Fwd | 5'-CACCTGCGCGTGTTCGTAGAGTTG-3' | SEQ ID NO: 66 |
| MRS2S Fwd | 5'-CACCTGAACTTGTGCACGTCATTT-3' | SEQ ID NO: 67 |

Combinations of PCR primers used to generate the MRS2 promoter fragments were as follows:

| Primer Pair | Product | Size | Location on SEQ ID NO: 2 |
|---|---|---|---|
| MRS2M Fwd + MRS2 Rev | MRS2M | 1949 | 921 to 2869 |
| MRS2S Fwd + MRS2 Rev | MRS2S | 957 | 1913 to 2869 |

The promoter corresponding to the cDNA 2D14 was designated as MRS3 (SEQ ID NO: 3). MRS3 was amplified out of Genome Walker library EcoRV by PCR with primers 2D14DS1,5'-ATGGGTTTGCGGGTATGGGTAGTGGTA-3' (SEQ ID NO: 53) and 2D14GSP5,5'-ACACCACCAGGT-TCACGGCGAGGAACAG-3' (SEQ ID NO: 54). Att sites were added to MRS3 by PCR amplifying the product of the primary reaction with primers consisting of ½ att and ½ gene-specific sequence, 2D14DS3, 5'-ACAAAAAAGCAG-GCTGCGGGTATGGGTAG-3' (SEQ ID NO: 55) and 2D14DS5,5'-ACAAGAAAGCTGGGTTGCTCGATCA-CAACA-3' (SEQ ID NO: 56). The full attB1 and attB2 sites were added by using primers attB1 (SEQ ID 43) and attB2 (SEQ ID NO: 44).

The promoter corresponding to the cDNA 4H19 was designated as MRS4 (SEQ ID NO: 4). MRS4 was amplified out of Genome Walker library DraI with primers 4H19GSP3,5'-TCTTTCTTGTGCACCGCCGAAGC-3' (SEQ ID NO: 57) and 4H19profor, 5'-ACCCGATAACGAGTTAACGATAT-GAACTGG-3' (SEQ ID NO: 58) followed by amplification with nested primers 4H19GSP4,5'-TGCACTCACACCGC-CGATGATGG-3' (SEQ ID NO: 59) and 4H19profor (SEQ ID NO: 58). Att sites were added to MRS4 by PCR amplifying the product of the primary reaction with primers consisting of ½ att and ½ gene-specific sequence, 4H19proforB1, 5'-ACAAAAAAGCAGGCTAACGATATGAACTGG-3' (SEQ ID NO: 60) and 4H19 prorevB2,5'-ACAA-GAAAGCTGGGTCTTCACGAGTTCGGT-3' (SEQ ID NO: 61). Each promoter with attB1 and attB2 ends was recombined into plasmid pDONR 201 (Life Technologies Cat. No. 11798-014), a donor vector with attP recombination sites, using the BP clonase mix of recombination enzymes (Life Technologies Cat. No. 11789-013). In this entry vector each promoter was directionally cloned with the 5' end of the promoter adjacent to the attL1 site and the 3' end adjacent to the attL2 site. A separate entry vector was made for each of the four promoters.

Destination Vectors

A Binary destination vector, useful for plant transformation, was constructed in the following manner. A recombination fragment (rf) containing lambda bacteriophage attachment-R (attR) sites flanking a chloramphenicol resistance gene and a controlled cell death (ccd) gene was obtained from Invitrogen (Cat. No. 11828-019). Oligonucleotides were obtained to amplify the rf cassette by PCR, incorporating a flanking 5' BclI site, rfBclI, 5'-TGCCCGTATGATCAA-CAAGTTTGTACAAAA-3' (SEQ ID NO: 62) and a 3' EcoRV site, rfEcoRV, 5'-CCAGACCGATATCAAC-CACTTTGTACAAGA-3' (SEQ ID NO: 63) into the cassette. The addition of these unique restriction sites made it possible to directionally subclone the recombination fragment in front of the β-glucouronidase (GUS) gene and nopaline synthase (nos) terminator (rf::gus::nos) to produce an intermediate donor vector. The expression cassette (rf::gus::nos) was removed from the donor vector by endonuclease digestion using KpnI and gel purification of the ~3 kb fragment. A recipient binary vector (Negrotto et al., 2000 Plant Cell Reports 19: 798-803) was prepared for ligation of the expression cassette by endonuclease digestion using KpnI and dephosphorelated using calf intestine phosphatase (CIP). The expression cassette was then subcloned into the KpnI site within the T-DNA region, near the right border of a binary plasmid. The T-DNA region of the final binary destination vector harbored the recombination expression cassette followed by a plant selectable marker expression cassette comprising the maize Ubiquitin promoter driving the phosphomannose isomerase gene and nos terminator (Negrotto et al., 2000 Plant Cell Reports 19: 798-803). The root-specific promoters, MRS1L, MRS1S, MRS2L, MRS2M, MRS2S, and MRS3, were each cloned into the final binary recombination vector in front of the GUS coding sequence. Thus, six binary vectors were made, MRS1 L-GUS, MRS1S-GUS, MRS2L-GUS, MRS2M-GUS, MRS2S-GUS, and MRS3-GUS.

Example 6

Transient Expression in Maize Directed by Root-Specific Promoters

Maize seeds were germinated and grown in the dark under sterile conditions for seven days. Root tissue was cut into 1 cm segments with sterile razor blades and arranged onto agarose plates prepared with 2JMS+AG media (JMS majors, SH minors, MS iron, 2% sucrose, 5 mg/ml dicamba, G5 additions, 10 mg/ml AgNO$_3$). Five micrograms of DNA from vectors comprising MRS1 L-GUS, MRS1S-GUS, MRS2L-GUS, and MRS3-GUS was precipitated onto (<1 μm) gold carriers and spotted onto micro-carriers for bombardment at 650 psi as described (Wright et al. 2001, Plant Cell Reports, 20: 429-436). Fragment DNA was precipitated onto gold microcarriers (<1 μm) as described in the DuPont Biolistics Manual. Genes were delivered to the target tissue cells using the PDS-1000He Biolistics device. The approximate settings on the device were as follows: 8 mm between the rupture disk and the macrocarrier, 1 mm between the macrocarrier and the stopping screen and 7 cm between the stopping screen and the target. The plates were shot twice with DNA-coated particles using 650 psi-rupture disks. To reduce tissue damage from the shock wave of the helium blast, a stainless steel mesh, with 200 openings per lineal inch horizontally and vertically (McMaster-Carr, New Brunswick, N.J.), was placed between the stopping screen and the target tissue. Roots were cultivated on the plates for 48 hrs in the dark at 25° C. Expression of GUS was visualized by staining with 100 mM NaPO$_4$, 0.5 mM Potassium Ferricyanide, 0.5 mM Potassium Ferrocyanide, 10 mM EDTA pH 8.0, 0.5 mg/ml X-Gluc, 0.1% Triton X-100. Table 3 shows the relative levels of GUS expression of the root-specific promoter constructs compared to a construct with the constitutive maize ubiquitin promoter driving expression of GUS, UbiP-GUS. A wildtype (Wt) maize plant was used as the negative control. GUS activity is characterized as high (+++), medium (++), low (+), or absent (−). Results indicate that promoters of the invention function in plant cells and drive the expression of a heterologous coding sequence at comparable levels to a constitutive promoter.

TABLE 3

Results of Transient Expression of GUS in Maize Roots.

| Construct | Relative GUS Expression Levels |
|---|---|
| Wt | − |
| UbiP-GUS | ++ |
| MRS1L-GUS | ++ |
| MRS1S-GUS | ++ |
| MRS2L-GUS | ++ |
| MRS3-GUS | ++ |

Example 7

Expression of Gus in Stably-Transformed Corn and Rice Directed by Root-Specific Promoters Maize and rice plants were transformed with expression cassettes comprising promoters of the invention operably linked to the GUS coding sequence. GUS activity in stably transformed maize and rice tissues was measured by a fluorometric assay. Plant tissue was ground in extraction buffer (50 mM Na$_2$HPO$_4$ pH 7.0, 5 mM DTT, 1 mM NA$_2$ EDTA, 0.1% Sarcosyl, 0.1% Triton-X). The reaction was carried out with approximately one part tissue extract to 5 parts assay buffer (extraction buffer with 47 mM 4-methylumbelliferyl-glucuromide) at 37° C. and stopped with 2% Na$_2$CO$_3$ at multiple time points. The activity was measured in a Tecan Spectrafluor Plus at 365 nm excitation and 455 nm emission calibrated with 4-MU standards diluted in Na$_2$CO$_3$. The slope of MU fluorescence verses time gives the activity of the GUS enzyme. Protein concentrations were measured by BCA assay (Pierce Cat. Nos. 23223 and 23224) and Gus activity was normalized for protein concentration. Gus activity was characterized as high (+++), medium (++), low (+), or absent (−) and data from 12 to 31 single copy transgenic maize plants or 7 single copy transgenic rice plants were averaged for each promoter construct. Results shown in Tables 4 and 5 demonstrate that GUS activity in transgenic plants comprising an expression cassette that comprises a promoter of the invention was confined specifically to the roots.

TABLE 4

GUS Expression in Tissues Excised from Transgenic Maize Plants.

| | GUS Activity in Designated Maize Tissue | | | | |
|---|---|---|---|---|---|
| Promoter | Root | Leaf | Silk | Pollen | Kernel |
| UbiP | +++ | +++ | +++ | +++ | +++ |
| MRS1L | + | − | − | − | − |
| MRS1S | + | − | − | − | − |
| MRS2L | + | − | − | − | − |
| MRS3 | + | − | − | − | − |

TABLE 5

GUS Expression in Tissues Excised from Transgenic Rice Plants.

| | GUS Activity in Designated Rice Tissue | |
|---|---|---|
| Promoter | Root | Leaf |
| Wildtype | − | − |
| UbiP | +++ | +++ |
| MRS2L | +++ | − |
| MRS2M | +++ | − |
| MRS2S | +++ | − |

Example 8

Expression of Insecticidal Toxin Using Root-Specific Promoter

Maize plants were transformed with an expression cassette comprising the MRS3 promoter operatively linked to a heterologous coding sequence that encodes a modified Cry3A toxin (U.S. Application No. 60/316,421). Excised roots of transformed plants expressing the insecticidal toxin were bioassayed against western corn rootworm and were observed to be insecticidal. Transformed plants comprising the MRS3-modified Cry3A expression cassette were resistant to corn rootworm larval feeding damage.

It will be recognized by those skilled in the art that the promoters of the present invention can be operably linked to other heterologous coding sequences that encode toxins active against corn rootworm, for example, the PS149B1 proteins (Moellenbeck et al. 2001, Nature Biotechnology 19: 668-672), a modified Cry3Bb toxin (U.S. Pat. No. 6,063, 597), the *Diabrotica* toxins disclosed in U.S. Pat. No. 6,281, 413, or the Vip1-Vip2 toxin (U.S. Pat. No. 5,872,212).

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious to persons skilled in the art that certain changes and modifications may be practiced within the scope of the present invention.

What is claimed is:

1. An isolated nucleic acid molecule which codes for a promoter capable of directing root-specific transcription in a plant, wherein the promoter comprises the nucleotide sequence set forth in SEQ ID NO:4.

2. An expression cassette comprising the nucleic acid molecule of claim 1 operably linked to a heterologous coding sequence, which is operably linked to a 3'-untranslated region including a polyadenylation signal.

3. The expression cassette according to claim 2, wherein the heterologous coding sequence is selected from the group consisting of insecticidal coding sequences, nematicidal coding sequences, herbicide tolerance coding sequences, anti-microbial coding sequences, antifungal coding sequences, anti-viral coding sequences, abiotic stress tolerance coding sequences, nutritional quality coding sequences, visible marker coding sequences, and selectable marker coding sequences.

4. The expression cassette according to claim 3, wherein the insecticidal coding sequence encodes a toxin active against a coleopteran pest.

5. The expression cassette according to claim 4, wherein the coleopteran pest is a species in the genus *Diabrotica*.

6. The expression cassette according to claim 3, wherein the visible marker is beta-glucuronidase.

7. A recombinant vector comprising the expression cassette of claim 2.

8. The recombinant vector according to claim 7, wherein the vector is a plasmid.

9. A transgenic plant cell comprising the expression cassette of claim 2.

10. A transgenic plant comprising the plant cell of claim 9.

* * * * *

SEQUENCE LISTING

<160> NUMBER OF SEQ ID NOS: 67

<210> SEQ ID NO 1
<211> LENGTH: 1392
<212> TYPE: DNA
<213> ORGANISM: Zea mays
<220> FEATURE:
<221> NAME/KEY: promoter
<222> LOCATION: (1)..(1392)
<223> OTHER INFORMATION: MRS1L
<220> FEATURE:
<221> NAME/KEY: promoter
<222> LOCATION: (603)..(1392)
<223> OTHER INFORMATION: MRS1S
<220> FEATURE:
<221> NAME/KEY: CAAT_signal
<222> LOCATION: (1251)..(1254)
<220> FEATURE:
<221> NAME/KEY: TATA_signal
<222> LOCATION: (1288)..(1295)

<400> SEQUENCE: 1

```
gaacatgacg gatgaagaat cactattgtt ttcttctttg cgtagaagat aatactcctc      60
ctgtcctaaa ttaatatttg tttaaacttt ttattggatt catgtaataa ttaatgtatg     120
tgttttatat atatgtctag atttataatt attcatatga atatggacat aaaaatctag     180
ggctaaaacg actactattt tgaaacggaa ggagtagtaa tttatttaag cggaggggaa     240
ccatgatggg ctagtgattt aatttacata tatattggtg ttttgggctc ttacatgaga     300
agatctagtt aactgctgtt actgaatagc gaagacaaat atataattta agctccccaa     360
ctgctagtga ttctgttaac aaataatgtt tattgtgatt ttaacaacag cccgtctagc     420
tcagtcggta gagcgcaagg ctcttaacct tgtggtcgtg ggttcgagcc ccacggtggg     480
cgctttgaga tgtttatttt ttgttgactt ttgcttggtt gcgtgggatt tccgagaaaa     540
aaaaggtact acaggtgttt taaactggca acctttggag cgtcgaggcg acgtgcattt     600
gcgtagttga agcttacaaa gttgcatact tgcatatgag atgattgccg gacatgaagc     660
ggataacgtt ttaaactggc aacaatatct tgctgtttca aattcaggcg tgggaagcta     720
cgcgccctgg acggcgtgta aagagccagc atcggcatca ttgtcaaacg atcgacaagg     780
gcaagaaatt ccaaatatat tttattaatc caaaagaagg cacaaattag tttggttttt     840
agtatgtgtg gcggaggaaa tcttgaggac gaacgtatca aaggaggcac aagataatag     900
tttgacgcgc gcgggtagaa gttgcagaag acagtgggta cggtcttatc ctaataaaat     960
aaaataaaac tatagtctat agtgtgtcaa atgtcaacaa gaggaagggc cagccaaatt    1020
agcagaggaa gacaagcaga gcacgcctta ttagcttgct tatttgtatc gtggtggtgt    1080
gtacttgtta attactggca cgcattatca acaatgcagt tctggatgtg aatctagaca    1140
aacatttgtc taggttccgc acgtataatt ttttttcttt tttttggggg aacggaagc     1200 tgtaataaac gaaactagga acgaaagcaa ccgccgcgcg catgtttttg caatagatta    1260
cggtgacctt gatgcaccac cgcgtgctat aaaaaccagt gtccccgagt ctactcatca    1320
accaatccat aactcgaaac cttttcttgt gctctgtctg tgtgtttcca aagcaaacga    1380
aagagctcga gg                                                        1392
```

<210> SEQ ID NO 2
<211> LENGTH: 2869
<212> TYPE: DNA
<213> ORGANISM: Zea mays
<220> FEATURE:

```
<221> NAME/KEY: promoter
<222> LOCATION: (1)..(2869)
<223> OTHER INFORMATION: MRS2
<220> FEATURE:
<221> NAME/KEY: promoter
<222> LOCATION: (921)..(2869)
<223> OTHER INFORMATION: MRS2-M
<220> FEATURE:
<221> NAME/KEY: promoter
<222> LOCATION: (1913)..(2869)
<223> OTHER INFORMATION: MRS2-S
<220> FEATURE:
<221> NAME/KEY: CAAT_signal
<222> LOCATION: (2563)..(2566)
<220> FEATURE:
<221> NAME/KEY: TATA_signal
<222> LOCATION: (2745)..(2751)

<400> SEQUENCE: 2
```

| | | | | | |
|---|---|---|---|---|---|
| ggcttgactt | tgcctagtgt | tggagaaaaa | acactcggca | aagagctctt | tgccgagtgt       60 |
| tgtatttgtg | acactcggca | aagagcccct | tgccgagtgt | caaaaaaaga | cactcggtaa      120 |
| agaaactctt | tgtcgagtgt | caaaaataaa | acactcggca | aaggtcttct | tcgccgagtg      180 |
| ttttcttttta | ccgagggttt | tttgtgtggc | actcggcaaa | gagcttttg | ccgagtgccc      240 |
| gaaataaaac | actcggcaaa | gaatatgaca | ctcggcaaag | agccaaattt | cggtagtgaa      300 |
| tctgcttgat | gaataaagct | tatatattgt | tcgaaatatg | tgtgcatatt | gttctaatat      360 |
| cagattttgt | tatgagtcat | atttcatttt | catacacgtc | gtttgcaaat | gcactacata      420 |
| aaacataatt | aattgaggca | acgatccata | tacatttgag | acgtagaatt | actagtattc      480 |
| atgcatgata | catttgacgc | aattatccat | aattaattga | tcggcaacgg | ctagcttcca      540 |
| accgttagct | agtccatgta | gaaggcacta | aacgtctcta | gtggcacgcc | atacatattg      600 |
| tcggttcctg | tccaaaaaac | tctaccacct | ttcaatagct | cttttgggct | cgagggctat      660 |
| aaataaatag | caccacagtg | ggctatttct | caagttttgt | gctgagaaac | atagcaagag      720 |
| aattgagact | ccgatctatt | agttcttaga | catctaagtg | ctttaaggtt | actcggtgat      780 |
| tcgtgtaggt | gttttgcaaa | gtacttaagt | cagttagacc | gtcactataa | cacttgctct      840 |
| aggttatgcc | tagttgagct | agacaccctc | aaacggtcaa | accttgatg | cttgtgcgca      900 |
| ccattatatg | catcgacact | tgcgcgtgtt | cgtagagttg | taccaggaag | ggttgtatct      960 |
| tgtgagatca | cactaaccac | gtttatgctg | cggcctccac | cgtacactag | agcgaacgag     1020 |
| gtcatgaagt | ttcagtcaga | agttcgatag | tgaagacaac | caagagcatc | cgagagaggc     1080 |
| caaatacgga | gcgccactta | tgagtggaga | aggctcgtga | ctatctgcgg | agttacctgg     1140 |
| ctaggagctt | ggccctcgcg | tgggctaccc | tttgcgtagg | ggttccgacg | aggattagga     1200 |
| agaagcttac | atatttcttg | ataccttagt | aaaaaatatc | agcgtgtcca | catgacttta     1260 |
| tatctctatc | tcatttaagc | ttctgcattt | atattgctaa | atttggttgt | gtgctttacc     1320 |
| tttcctaact | tagttacatg | ctagttagta | ggactgaaaa | cttaggttac | ataactacat     1380 |
| tatagagata | gcaacactta | aacaaaacct | tagttgcact | agctttcttg | gttatatatt     1440 |
| tgtataggtt | ttgcttaaga | gattcaatta | gaagcctaaa | ttagcgtgaa | tagttgttct     1500 |
| gattcatccc | tctcttagat | gcccacgttc | cttctagaga | gcacttgatc | ctgcttgcac     1560 |
| ggatgaaggg | gtagtgagtg | agtgacacac | ttgcatgggt | gctctaacaa | ggaccagtga     1620 |
| ggagtgttga | ctctctgata | tctcgacaaa | acgtcgtcat | gttaataatc | cttctttact     1680 |
| ttgaacattt | acattcaagc | aattcaattc | ttgttttgta | ttactataat | tgtcatgctg     1740 |
| aaatatggtt | gaaacgcagt | aggacgtaag | aaattttatg | atataattga | aaattttatgt    1800 |

```
atgcttaaag gatgaagtgg gctattcgat agcattgaac tattataaga agcattattt    1860
taatataatt tacctttctt ttggacatct tagtcttgta ctaaactatt tttgaacttg    1920
tgcacgtcat ttatgtttct tatacttgga gcttgccaaa tgttttctgg gctttgtgaa    1980
gtgcatgaag cactcggcaa aacagctatc tccggtggtg aagagttggg gtaaatgtat    2040
tagtattagt acactctttt tcataaacaa gcggaaccat ctagccaaca gtacgtcata    2100 caaaagggc acccaccgtt gtttgtgggc atgcttctta agcaaattca agcctctaac     2160
tttgaatgtt ccaactgaac ataataaatg ttgacccgat cagggacaga gctaaagcaa    2220
attttagtga ttgcaattgc cttctgagcg cattcagttt tacgatgagg atacgtttag    2280
agtaaaattt tgatcatttc attctaccat gcaagggtgc acccgtaccc accgctatat    2340
gcatagctct gcgcttggat cccgtgaagt gcagaaaaat acttcaactg ttcaacaact    2400
tgggcgtcca ccgtccatgc atcaccatga tacctctgct gatgtttagc actcgatcac    2460
gttactagat acaagcagcc aacccatatg acaagttcct aactgaataa aaatgatcaa    2520
ccatcaagcg agaacaagca tcaacatgca tccaccagtg gagcaatctt ggccacttgc    2580
gctgttgaaa cttggttctg gagtaccacc caaatattag tggatcaaat ccagatcagc    2640
catctaatta ataatcgccc tcacatgcac tcatgctcac gggaatgtaa actcacacaa    2700
caacactgct aatacactaa tcggcactgc gccgatggtt ctcctataaa tgcaacaatc    2760
aagcgccacc acgaaccatc acaagcgctt agtgatcagt taatactaag ggcaggcaca    2820
cctctgcttc gcgctagtga tcaagcaagt gctttctgta ctctgcagc                2869

<210> SEQ ID NO 3
<211> LENGTH: 973
<212> TYPE: DNA
<213> ORGANISM: Zea mays
<220> FEATURE:
<221> NAME/KEY: promoter
<222> LOCATION: (1)..(973)
<223> OTHER INFORMATION: MRS3
<220> FEATURE:
<221> NAME/KEY: TATA_signal
<222> LOCATION: (840)..(847)

<400> SEQUENCE: 3
ggctgcgggt atgggtagtg gtagaacaaa cccatgccca cgtacccgtt gggtttccat      60
ttgaacccat taacaaactc atgggtacag aaattgaccc aaacccatac cctaatagag     120
caaaaaccca ccgggtttcg ggtaccgggt acccattgcc atctctacga gtgaccgaca     180
gaaagcactc ggcaaagagc tggattcggg tagcgcgggg ttattttga ggtctaaaat      240 tgaagttgat atgcccttcg gaacgaatga ccccaaaatt ggtgtctgaa atgttccttt     300
gaatgctgtt ccttaaaaaa acgtttcgat gctaaacaaa agcataggaa atatatagtt     360
ttgctggtat acctgcacca tgcatgcgtc cgcgctattc ctctgcaggc gccttggtct     420
tgtgcgtaca tgcctatgga tgatcacagg cacgccacat ttcattctta atcactactt     480
aattgacatc taatgccctc tgctcaactt gcgcacgcta cgcaccgtat gatacgccaa     540
gatcccaagc taaataaaca cccaatcgtc atataaaaac aagtgtcagt gcgagccagc     600
ccatgcatgc gcagcgatct tggccattg cggagccaac ccaagccgag cgagcagaaa      660
atatgcgata ccgtatgagg gaaaacacta gttattatac gaggtagcta gcaataatac     720
agatcggact cttcgcaacg taaccggctt cttcacatgc acatcatatg atggccgcct     780
gggttcacat gaacgctccc gtgcctagtt gcaccgattt cttaatcccg agcatggact     840
ataaaatccc ctggtaacac cgtgatcaaa gcatcgcaaa caagctagct aatcacttgt     900
```

```
caagaacaag agctctctac ctgcattggc tagcgtgatc cgcgaggtag ctggctgctt      960
gttgtgatcg agc                                                        973

<210> SEQ ID NO 4
<211> LENGTH: 687
<212> TYPE: DNA
<213> ORGANISM: Zea mays
<220> FEATURE:
<221> NAME/KEY: promoter
<222> LOCATION: (1)..(687)
<223> OTHER INFORMATION: MRS4
<220> FEATURE:
<221> NAME/KEY: CAAT_signal
<222> LOCATION: (556)..(559)
<220> FEATURE:
<221> NAME/KEY: TATA_signal
<222> LOCATION: (602)..(608)

<400> SEQUENCE: 4
acgatatgaa ctggtatgtg tttgtggttg agttgcgtta gcagctgatg ctatgtccag       60
gttttccttt aattagtcat gttactcatg catagtttct cggtctaaat tccgttgtaa      120
aacgggctat atattttcct taatttcatt gctaagtgaa tcgggcgtga gctcctagct      180
ctttttcgaa ggttcttcca aaggaagata catagcacat gtagcaatgg atcccaagag      240
atcttttgac actcatctca atatctcata actatttcag aaactgtcgc tgtcagccat      300
cgacaggtgt ccactgattg cacctcagag gatccccact acgcataaaa ttaaaggcga      360
tcgactcact gaaacctatc tccctagtag gttaggcata acaaagtgtt agcgcctcaa      420
tggccaccca caaaaaggat caaaagcatg agaatccagt ggtcgtctgg ctcaaagata      480
agtgggtgca gatatgcgag aatccacgac gcaaccaaag aatcctccct tcaccaatta      540
acaatccctg caggccaatc gctcgcacag acttgcgtga ttcagttgac gagaagatgc      600
ctataaaaga aaggaaaatt ggccaagcta aggcctcact agtgtgttcc cactcacacc      660
gaactcgtga agcacagctt ccatcgt                                          687

<210> SEQ ID NO 5
<211> LENGTH: 609
<212> TYPE: DNA
<213> ORGANISM: Zea mays
<220> FEATURE:
<221> NAME/KEY: misc_feature
<222> LOCATION: (1)..(589)
<223> OTHER INFORMATION: 22P8 cDNA
<220> FEATURE:
<221> NAME/KEY: misc_feature
<222> LOCATION: (1)..(589)
<223> OTHER INFORMATION: n = unknown base
<220> FEATURE:
<221> NAME/KEY: CDS
<222> LOCATION: (71)..(589)

<400> SEQUENCE: 5
gcgtccgtaa ctcgaaacct tttcttgtgc tctgtctgtg tgtttccaaa gcaaacgaaa       60
gagctcgagg atg tct tgc agc tgc gga tca agc tgc aac tgc gga tca         109
             Met Ser Cys Ser Cys Gly Ser Ser Cys Asn Cys Gly Ser
               1               5                  10 agc cgc aac tgc ggc aag atg tac cct gac ctg gag gag aag agc ggc        157
Ser Arg Asn Cys Gly Lys Met Tyr Pro Asp Leu Glu Glu Lys Ser Gly
         15                  20                  25 ggg ggc gct cag gcc agc gcc gcc gcc gtc ctc ggc gtt gcc cct gag        205
Gly Gly Ala Gln Ala Ser Ala Ala Ala Val Leu Gly Val Ala Pro Glu
 30                  35                  40                  45
```

```
acg aag aag gcg gcg cag ttc gag gcg gcg ggc gag tcc ggc gag gcc    253
Thr Lys Lys Ala Ala Gln Phe Glu Ala Ala Gly Glu Ser Gly Glu Ala
                 50                  55                  60 gcc cac ggc tgc agc tgc ggt gac agc tgc aag tgc agc ccg tgc aac    301
Ala His Gly Cys Ser Cys Gly Asp Ser Cys Lys Cys Ser Pro Cys Asn
 65                  70                  75 tgc nnn tcc tgc tgc gtt gtt tcg ttt gcg gca tgc atg cct gtc act    349
Cys Xaa Ser Cys Cys Val Val Ser Phe Ala Ala Cys Met Pro Val Thr
         80                  85                  90 ttt ttt acg tac tgt ctg ctt tgt gct tgt ggc gtg tca aga ata aag    397
Phe Phe Thr Tyr Cys Leu Leu Cys Ala Cys Gly Val Ser Arg Ile Lys
 95                 100                 105 gat gga gcc atc gtc tgg tct ggc tct ggc tct ccg cca ggc atg ctt    445
Asp Gly Ala Ile Val Trp Ser Gly Ser Gly Ser Pro Pro Gly Met Leu
110                 115                 120                 125 ggt gtc ggt tct gtt gtg ctt gtg ttg gtg cat gta atc gta tgg cat    493
Gly Val Gly Ser Val Val Leu Val Leu Val His Val Ile Val Trp His
                130                 135                 140 cgt tac aca cca tgc atc tct gat ctc tgt gcg cta gtg tgt gtg act    541
Arg Tyr Thr Pro Cys Ile Ser Asp Leu Cys Ala Leu Val Cys Val Thr
                145                 150                 155 atg tcc ctg nnn cga ttg gct caa tat ata caa tac tgt ttt acc aaa    589
Met Ser Leu Xaa Arg Leu Ala Gln Tyr Ile Gln Tyr Cys Phe Thr Lys
            160                 165                 170 aaaaaaaaaa aaaaaaaaa                                                609

<210> SEQ ID NO 6
<211> LENGTH: 173
<212> TYPE: PRT
<213> ORGANISM: Zea mays
<220> FEATURE:
<221> NAME/KEY: misc_feature
<222> LOCATION: (79)..(79)
<223> OTHER INFORMATION: The 'Xaa' at location 79 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (161)..(161)
<223> OTHER INFORMATION: The 'Xaa' at location 161 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1)..(173)
<223> OTHER INFORMATION: 22P8

<400> SEQUENCE: 6

Met Ser Cys Ser Cys Gly Ser Ser Cys Asn Cys Gly Ser Ser Arg Asn
 1               5                  10                  15

Cys Gly Lys Met Tyr Pro Asp Leu Glu Glu Lys Ser Gly Gly Gly Ala
                 20                  25                  30

Gln Ala Ser Ala Ala Ala Val Leu Gly Val Ala Pro Glu Thr Lys Lys
             35                  40                  45

Ala Ala Gln Phe Glu Ala Ala Gly Glu Ser Gly Glu Ala Ala His Gly
         50                  55                  60

Cys Ser Cys Gly Asp Ser Cys Lys Cys Ser Pro Cys Asn Cys Xaa Ser
 65                  70                  75                  80

Cys Cys Val Val Ser Phe Ala Ala Cys Met Pro Val Thr Phe Phe Thr
                 85                  90                  95

Tyr Cys Leu Leu Cys Ala Cys Gly Val Ser Arg Ile Lys Asp Gly Ala
            100                 105                 110

Ile Val Trp Ser Gly Ser Gly Ser Pro Pro Gly Met Leu Gly Val Gly
```

```
                    115                 120                 125
Ser Val Val Leu Val Leu Val His Val Ile Val Trp His Arg Tyr Thr
        130                 135                 140

Pro Cys Ile Ser Asp Leu Cys Ala Leu Val Cys Val Thr Met Ser Leu
145                 150                 155                 160

Xaa Arg Leu Ala Gln Tyr Ile Gln Tyr Cys Phe Thr Lys
                165                 170

<210> SEQ ID NO 7
<211> LENGTH: 766
<212> TYPE: DNA
<213> ORGANISM: Zea mays
<220> FEATURE:
<221> NAME/KEY: misc_feature
<222> LOCATION: (1)..(766)
<223> OTHER INFORMATION: n = unknown base
<220> FEATURE:
<221> NAME/KEY: misc_feature
<222> LOCATION: (1)..(766)
<223> OTHER INFORMATION: 10B21 cDNA
<220> FEATURE:
<221> NAME/KEY: CDS
<222> LOCATION: (76)..(744)

<400> SEQUENCE: 7
tcagttaata ctaagggcag gcacacctct gcttcgcgct agtgatcaag caagtgcttt      60
ctgtactctg cagca atg gca ggc aag gcc tcg gtc gcg ctg ttc ctc gcc     111
                 Met Ala Gly Lys Ala Ser Val Ala Leu Phe Leu Ala
                   1               5                  10 gtg aac ctg gtg gtg ttc gcc atg gcc agc gcc tgc ggt ggc aac tgc     159
Val Asn Leu Val Val Phe Ala Met Ala Ser Ala Cys Gly Gly Asn Cys
         15                  20                  25 ccc acg ccg acc ccg tcc acc ccg tcg acg ccg acc ccg acg ccg gcc     207
Pro Thr Pro Thr Pro Ser Thr Pro Ser Thr Pro Thr Pro Thr Pro Ala
         30                  35                  40 tcg ttc ggc aag tgc ccc cgc gac gcg ctc aag ctg ggc gtg tgc gcc     255
Ser Phe Gly Lys Cys Pro Arg Asp Ala Leu Lys Leu Gly Val Cys Ala
 45                  50                  55                  60 aac gtg ctg gga ctg atc aag gcc aag gtg ggc gtg ccg ccc acg gag     303
Asn Val Leu Gly Leu Ile Lys Ala Lys Val Gly Val Pro Pro Thr Glu
                 65                  70                  75 cca tgc tgc ccg ctg ctg aag gga ctc gtc gac ctc gag gcc gcc gtg     351
Pro Cys Cys Pro Leu Leu Lys Gly Leu Val Asp Leu Glu Ala Ala Val
             80                  85                  90 tgc ctc tgc acc gcc atc aag ggc gag gtc ctc gga atc aag ctc aac     399
Cys Leu Cys Thr Ala Ile Lys Gly Glu Val Leu Gly Ile Lys Leu Asn
         95                 100                 105 ctg ccc gtc gac ctc agc ctc atc ctc aac cac tgc ggc aag act gtg     447
Leu Pro Val Asp Leu Ser Leu Ile Leu Asn His Cys Gly Lys Thr Val
    110                 115                 120 ccc acc gga ttc aaa tgc ctc nnn gct agc cgc gag cat gcg gat ata     495
Pro Thr Gly Phe Lys Cys Leu Xaa Ala Ser Arg Glu His Ala Asp Ile
125                 130                 135                 140 tat gtg ttc ttt tgg ttg cca ttc gcc tgc agg ctt ctt gtc gtt tgc     543
Tyr Val Phe Phe Trp Leu Pro Phe Ala Cys Arg Leu Leu Val Val Cys
                145                 150                 155 tac tta tta agc gag tgc nnn ctc tgc atg cat gac tac gtc ctt tgc     591
Tyr Leu Leu Ser Glu Cys Xaa Leu Cys Met His Asp Tyr Val Leu Cys
            160                 165                 170 atg ttg atg agc agc ttt cgc ttt tgg gtg ttt gtt ttg tgt aag tgc     639
Met Leu Met Ser Ser Phe Arg Phe Trp Val Phe Val Leu Cys Lys Cys
        175                 180                 185
```

```
ttc gtc ctt tgc atc gac agt gtc cca gaa cta ttt gga ctg tta ttc      687
Phe Val Leu Cys Ile Asp Ser Val Pro Glu Leu Phe Gly Leu Leu Phe
    190                 195                 200 ttt tat ttg tat cca gca atc tgc ttg ata nnn aat aaa gct tat att      735
Phe Tyr Leu Tyr Pro Ala Ile Cys Leu Ile Xaa Asn Lys Ala Tyr Ile
205                 210                 215                 220 att tat tgg aaaaaaaaaa aaaaaaaaaa aa                                 766
Ile Tyr Trp
```

<210> SEQ ID NO 8
<211> LENGTH: 223
<212> TYPE: PRT
<213> ORGANISM: Zea mays
<220> FEATURE:
<221> NAME/KEY: misc_feature
<222> LOCATION: (132)..(132)
<223> OTHER INFORMATION: The 'Xaa' at location 132 stands for Lys, Asn,
    Arg, Ser, Thr, Ile, Met, Glu, Asp, Gly, Ala, Val, Gln, His, Pro,
    Leu, Tyr, Trp, Cys, or Phe.
<220> FEATURE:
<221> NAME/KEY: misc_feature
<222> LOCATION: (163)..(163)
<223> OTHER INFORMATION: The 'Xaa' at location 163 stands for Lys, Asn,
    Arg, Ser, Thr, Ile, Met, Glu, Asp, Gly, Ala, Val, Gln, His, Pro,
    Leu, Tyr, Trp, Cys, or Phe.
<220> FEATURE:
<221> NAME/KEY: misc_feature
<222> LOCATION: (215)..(215)
<223> OTHER INFORMATION: The 'Xaa' at location 215 stands for Lys, Asn,
    Arg, Ser, Thr, Ile, Met, Glu, Asp, Gly, Ala, Val, Gln, His, Pro,
    Leu, Tyr, Trp, Cys, or Phe.
<220> FEATURE:
<221> NAME/KEY: misc_feature
<222> LOCATION: (1)..(223)
<223> OTHER INFORMATION: 10B21

<400> SEQUENCE: 8

```
Met Ala Gly Lys Ala Ser Val Ala Leu Phe Leu Ala Val Asn Leu Val
1               5                   10                  15

Val Phe Ala Met Ala Ser Ala Cys Gly Gly Asn Cys Pro Thr Pro Thr
            20                  25                  30

Pro Ser Thr Pro Ser Thr Pro Thr Pro Thr Pro Ala Ser Phe Gly Lys
        35                  40                  45

Cys Pro Arg Asp Ala Leu Lys Leu Gly Val Cys Ala Asn Val Leu Gly
    50                  55                  60

Leu Ile Lys Ala Lys Val Gly Val Pro Pro Thr Glu Pro Cys Cys Pro
65                  70                  75                  80

Leu Leu Lys Gly Leu Val Asp Leu Glu Ala Ala Val Cys Leu Cys Thr
                85                  90                  95

Ala Ile Lys Gly Glu Val Leu Gly Ile Lys Leu Asn Leu Pro Val Asp
            100                 105                 110

Leu Ser Leu Ile Leu Asn His Cys Gly Lys Thr Val Pro Thr Gly Phe
        115                 120                 125

Lys Cys Leu Xaa Ala Ser Arg Glu His Ala Asp Ile Tyr Val Phe Phe
    130                 135                 140

Trp Leu Pro Phe Ala Cys Arg Leu Leu Val Cys Tyr Leu Leu Ser
145                 150                 155                 160

Glu Cys Xaa Leu Cys Met His Asp Tyr Val Leu Cys Met Leu Met Ser
                165                 170                 175

Ser Phe Arg Phe Trp Val Phe Val Leu Cys Lys Cys Phe Val Leu Cys
            180                 185                 190

Ile Asp Ser Val Pro Glu Leu Phe Gly Leu Leu Phe Pro Tyr Leu Tyr
        195                 200                 205
```

```
Pro Ala Ile Cys Leu Ile Xaa Asn Lys Ala Tyr Ile Ile Tyr Trp
    210                 215                 220
```

```
<210> SEQ ID NO 9
<211> LENGTH: 663
<212> TYPE: DNA
<213> ORGANISM: Zea mays
<220> FEATURE:
<221> NAME/KEY: misc_feature
<222> LOCATION: (1)..(654)
<223> OTHER INFORMATION: n=unknown base
<220> FEATURE:
<221> NAME/KEY: misc_feature
<222> LOCATION: (1)..(654)
<223> OTHER INFORMATION: 2D14 cDNA
<220> FEATURE:
<221> NAME/KEY: CDS
<222> LOCATION: (7)..(654)

<400> SEQUENCE: 9
```

```
cgagca atg gcg tcc aag gca ttc gcg ctg ttc ctg gcc gtg aac ctg        48
       Met Ala Ser Lys Ala Phe Ala Leu Phe Leu Ala Val Asn Leu
       1               5                   10 gtg gtg ctg ggc gta gcc aac gcc tgc acg tcc aac tgc tcg acc ccc        96
Val Val Leu Gly Val Ala Asn Ala Cys Thr Ser Asn Cys Ser Thr Pro
15                  20                  25                  30 tcg acg ccg acg ccg acg ccc acg ccg tcg tcg tcc ggc agg tgc ccc       144
Ser Thr Pro Thr Pro Thr Pro Thr Pro Ser Ser Ser Gly Arg Cys Pro
                35                  40                  45 cgc gac gcg ctc aag ttg ggc gtg tgc gcc aac gtg ctg ggc ctc atc       192
Arg Asp Ala Leu Lys Leu Gly Val Cys Ala Asn Val Leu Gly Leu Ile
            50                  55                  60 aag gct aag gtg ggc gcg ccg ccc gcg gag cca tgc tgc ccg ctg ctg       240
Lys Ala Lys Val Gly Ala Pro Pro Ala Glu Pro Cys Cys Pro Leu Leu
65                  70                  75 gag ggg ctc gtc gac ctg gag gcc gcc gcc tgc ctc tgc act gct atc       288
Glu Gly Leu Val Asp Leu Glu Ala Ala Ala Cys Leu Cys Thr Ala Ile
                80                  85                  90 aag ggc aac atc ctc ggc atc aac ctc aac ctg ccg gtc gat ctc agc       336
Lys Gly Asn Ile Leu Gly Ile Asn Leu Asn Leu Pro Val Asp Leu Ser
95                  100                 105                 110 ctc atc ctc aac tac tgc ggc agg acc gtg ccc acc ggc ttc aag tgc       384
Leu Ile Leu Asn Tyr Cys Gly Arg Thr Val Pro Thr Gly Phe Lys Cys
                115                 120                 125 nnn gcg cct ctc cgt ctc atc gcc ttg cgc tgc ctc cct tcc att cca       432
Xaa Ala Pro Leu Arg Leu Ile Ala Leu Arg Cys Leu Pro Ser Ile Pro
            130                 135                 140 tgc ata ttg cat ggt tcc gtt tca gtg acg cat ggt tcc gtt nnn ttg       480
Cys Ile Leu His Gly Ser Val Ser Val Thr His Gly Ser Val Xaa Leu
145                 150                 155 ctt tcc cac gta cga gag gta ctg cat gca tgc aac aca tgg ccg tac       528
Leu Ser His Val Arg Glu Val Leu His Ala Cys Asn Thr Trp Pro Tyr
                160                 165                 170 cgt acg tgc tct cga ttt gta att tcc cag cct ctt ccg tcc ttg tgt       576
Arg Thr Cys Ser Arg Phe Val Ile Ser Gln Pro Leu Pro Ser Leu Cys
175                 180                 185                 190 aca ttt gtt gta aag ggc tgg cga tca ctt cta cgc cgg tgc nnn nnn       624
Thr Phe Val Val Lys Gly Trp Arg Ser Leu Leu Arg Arg Cys Xaa Xaa
                195                 200                 205 gtt cca atc aag ttt cag tgt ttt gca tgc aaaaaaaaa                     663
Val Pro Ile Lys Phe Gln Cys Phe Ala Cys
            210                 215
```

```
<210> SEQ ID NO 10
```

-continued

```
<211> LENGTH: 216
<212> TYPE: PRT
<213> ORGANISM: Zea mays
<220> FEATURE:
<221> NAME/KEY: misc_feature
<222> LOCATION: (127)..(127)
<223> OTHER INFORMATION: The 'Xaa' at location 127 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (157)..(157)
<223> OTHER INFORMATION: The 'Xaa' at location 157 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (205)..(205)
<223> OTHER INFORMATION: The 'Xaa' at location 205 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (206)..(206)
<223> OTHER INFORMATION: The 'Xaa' at location 206 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1)..(216)
<223> OTHER INFORMATION: 2D14

<400> SEQUENCE: 10

Met Ala Ser Lys Ala Phe Ala Leu Phe Leu Ala Val Asn Leu Val Val
1               5                   10                  15

Leu Gly Val Ala Asn Ala Cys Thr Ser Asn Cys Ser Thr Pro Ser Thr
            20                  25                  30

Pro Thr Pro Thr Pro Thr Pro Ser Ser Ser Gly Arg Cys Pro Arg Asp
        35                  40                  45

Ala Leu Lys Leu Gly Val Cys Ala Asn Val Leu Gly Leu Ile Lys Ala
    50                  55                  60

Lys Val Gly Ala Pro Pro Ala Glu Pro Cys Cys Pro Leu Leu Glu Gly
65                  70                  75                  80

Leu Val Asp Leu Glu Ala Ala Cys Leu Cys Thr Ala Ile Lys Gly
                85                  90                  95

Asn Ile Leu Gly Ile Asn Leu Asn Leu Pro Val Asp Leu Ser Leu Ile
                100                 105                 110

Leu Asn Tyr Cys Gly Arg Thr Val Pro Thr Gly Phe Lys Cys Xaa Ala
            115                 120                 125

Pro Leu Arg Leu Ile Ala Leu Arg Cys Leu Pro Ser Ile Pro Cys Ile
        130                 135                 140

Leu His Gly Ser Val Ser Val Thr His Gly Ser Val Xaa Leu Leu Ser
145                 150                 155                 160

His Val Arg Glu Val Leu His Ala Cys Asn Thr Trp Pro Tyr Arg Thr
                165                 170                 175

Cys Ser Arg Phe Val Ile Ser Gln Pro Leu Pro Ser Leu Cys Thr Phe
            180                 185                 190

Val Val Lys Gly Trp Arg Ser Leu Leu Arg Arg Cys Xaa Xaa Val Pro
        195                 200                 205

Ile Lys Phe Gln Cys Phe Ala Cys
    210                 215

<210> SEQ ID NO 11
<211> LENGTH: 610
<212> TYPE: DNA
```

```
<213> ORGANISM: Zea mays
<220> FEATURE:
<221> NAME/KEY: misc_feature
<222> LOCATION: (1)..(610)
<223> OTHER INFORMATION: n=unknown base
<220> FEATURE:
<221> NAME/KEY: misc_feature
<222> LOCATION: (1)..(610)
<223> OTHER INFORMATION: 4H19 cDNA
<220> FEATURE:
<221> NAME/KEY: CDS
<222> LOCATION: (37)..(588)

<400> SEQUENCE: 11
actcacaccg aactcgtgaa gcacagcttc catcgt atg atg tcg agg aag agg       54
                                        Met Met Ser Arg Lys Arg
                                        1               5 aag aag agg ggc aaa gaa gaa gaa ggt gct gtg agc gaa gca ctg gtc      102
Lys Lys Arg Gly Lys Glu Glu Glu Gly Ala Val Ser Glu Ala Leu Val
        10                  15                  20 gtc gca ccg cca tca tcg gcg gtg nnn gtg cat gca gcg aag aag cat      150
Val Ala Pro Pro Ser Ser Ala Val Xaa Val His Ala Ala Lys Lys His
    25                  30                  35 gct tgc cat gcc gtc cgc cgg gag ctt cgg cgc cgc ggg ctg gtg gcg      198
Ala Cys His Ala Val Arg Arg Glu Leu Arg Arg Arg Gly Leu Val Ala
40                  45                  50 tgt gag cag gga tgc ttc ggc ggt gca caa gaa aga agg caa gtc tta      246
Cys Glu Gln Gly Cys Phe Gly Gly Ala Gln Glu Arg Arg Gln Val Leu
55                  60                  65                  70 tcg gca agg gaa ggc nnn gcc ttt ctt cca ggt ctc cct ctc tcc atc      294
Ser Ala Arg Glu Gly Xaa Ala Phe Leu Pro Gly Leu Pro Leu Ser Ile
            75                  80                  85 nnn atc att cta tgt gtt tgg agg agg ggg caa tcg atc gtt act tac      342
Xaa Ile Ile Leu Cys Val Trp Arg Arg Gly Gln Ser Ile Val Thr Tyr
        90                  95                  100 tgg tct cct gat cct nnn cgg tca tgt ctc cgt gtg tgt gtg tgt gcg      390
Trp Ser Pro Asp Pro Xaa Arg Ser Cys Leu Arg Val Cys Val Cys Ala
    105                 110                 115 ctc cat ctc cgt gtt gat ttc cag cta gaa nnn nnn cca gtt cag agt      438
Leu His Leu Arg Val Asp Phe Gln Leu Glu Xaa Xaa Pro Val Gln Ser
120                 125                 130 gaa tgt gtg agc gtg tgt gtg ttc aag tgt cag nnn gcg aac ctt gcg      486
Glu Cys Val Ser Val Cys Val Phe Lys Cys Gln Xaa Ala Asn Leu Ala
135                 140                 145                 150 ttg tat ttt gac cgt gtg agt cct gtg tat ttt cag ttg tct ggt gtg      534
Leu Tyr Phe Asp Arg Val Ser Pro Val Tyr Phe Gln Leu Ser Gly Val
            155                 160                 165 ttg tgt gtg agt atc tct gaa nnn gaa tgt aat gct ata tgt gtg ccc      582
Leu Cys Val Ser Ile Ser Glu Xaa Glu Cys Asn Ala Ile Cys Val Pro
        170                 175                 180 gtg caa aaaaaaaaa aaaaaaaaa aa                                       610
Val Gln <210> SEQ ID NO 12
<211> LENGTH: 184
<212> TYPE: PRT
<213> ORGANISM: Zea mays
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (76)..(76)
```

```
<223> OTHER INFORMATION: The 'Xaa' at location 76 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (87)..(87)
<223> OTHER INFORMATION: The 'Xaa' at location 87 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (108)..(108)
<223> OTHER INFORMATION: The 'Xaa' at location 108 stands for Lys, Asn,
      Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (129)..(129)
<223> OTHER INFORMATION: The 'Xaa' at location 129 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (130)..(130)
<223> OTHER INFORMATION: The 'Xaa' at location 130 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (146)..(146)
<223> OTHER INFORMATION: The 'Xaa' at location 146 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (174)..(174)
<223> OTHER INFORMATION: The 'Xaa' at location 174 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (1)...(184)
<223> OTHER INFORMATION: 4H19

<400> SEQUENCE: 12

Met Met Ser Arg Lys Arg Lys Lys Arg Gly Lys Glu Glu Glu Gly Ala
1               5                   10                  15

Val Ser Glu Ala Leu Val Val Ala Pro Pro Ser Ser Ala Val Xaa Val
            20                  25                  30

His Ala Ala Lys Lys His Ala Cys His Ala Val Arg Arg Glu Leu Arg
        35                  40                  45

Arg Arg Gly Leu Val Ala Cys Glu Gln Gly Cys Phe Gly Gly Ala Gln
    50                  55                  60

Glu Arg Arg Gln Val Leu Ser Ala Arg Glu Gly Xaa Ala Phe Leu Pro
65                  70                  75                  80

Gly Leu Pro Leu Ser Ile Xaa Ile Ile Leu Cys Val Trp Arg Arg Gly
                85                  90                  95

Gln Ser Ile Val Thr Tyr Trp Ser Pro Asp Pro Xaa Arg Ser Cys Leu
            100                 105                 110

Arg Val Cys Val Cys Ala Leu His Leu Arg Val Asp Phe Gln Leu Glu
        115                 120                 125

Xaa Xaa Pro Val Gln Ser Glu Cys Val Ser Val Cys Val Phe Lys Cys
    130                 135                 140

Gln Xaa Ala Asn Leu Ala Leu Tyr Phe Asp Arg Val Ser Pro Val Tyr
145                 150                 155                 160

Phe Gln Leu Ser Gly Val Leu Cys Val Ser Ile Ser Glu Xaa Glu Cys
                165                 170                 175

Asn Ala Ile Cys Val Pro Val Gln
```

-continued

```
                      180

<210> SEQ ID NO 13
<211> LENGTH: 24
<212> TYPE: DNA
<213> ORGANISM: Artificial Sequence
<220> FEATURE:
<223> OTHER INFORMATION: 22P8 cDNA RACE primer-1

<400> SEQUENCE: 13
cacactagcg cacagagatc agag                                            24

<210> SEQ ID NO 14
<211> LENGTH: 24
<212> TYPE: DNA
<213> ORGANISM: Artificial Sequence
<220> FEATURE:
<223> OTHER INFORMATION: 22P8 cDNA RACE primer-2

<400> SEQUENCE: 14
gcaccaacac aagcacaaca gaac                                            24

<210> SEQ ID NO 15
<211> LENGTH: 24
<212> TYPE: DNA
<213> ORGANISM: Artificial Sequence
<220> FEATURE:
<223> OTHER INFORMATION: 22P8 cDNA RACE primer-3

<400> SEQUENCE: 15
cagggtacat cttgccgcac ttgc                                            24

<210> SEQ ID NO 16
<211> LENGTH: 24
<212> TYPE: DNA
<213> ORGANISM: Artificial Sequence
<220> FEATURE:
<223> OTHER INFORMATION: 22P8 cDNA RACE primer-4

<400> SEQUENCE: 16
tgatccgcag ttgcagcttg atcc                                            24

<210> SEQ ID NO 17
<211> LENGTH: 23
<212> TYPE: DNA
<213> ORGANISM: Artificial Sequence
<220> FEATURE:
<223> OTHER INFORMATION: 10B21 cDNA RACE primer-1

<400> SEQUENCE: 17
catgctcgcg gctagcttag agg                                             23

<210> SEQ ID NO 18
<211> LENGTH: 23
<212> TYPE: DNA
<213> ORGANISM: Artificial Sequence
<220> FEATURE:
<223> OTHER INFORMATION: 10B21 cDNA RACE primer-2

<400> SEQUENCE: 18
acagtcttgc cgcagtggtt gag                                             23

<210> SEQ ID NO 19
<211> LENGTH: 23
<212> TYPE: DNA
<213> ORGANISM: Artificial Sequence
<220> FEATURE:
```

```
<223> OTHER INFORMATION: 10B21 cDNA RACE primer-3

<400> SEQUENCE: 19
tgaggctgag gtcgacgggc agg                                              23

<210> SEQ ID NO 20
<211> LENGTH: 23
<212> TYPE: DNA
<213> ORGANISM: Artificial Sequence
<220> FEATURE:
<223> OTHER INFORMATION: 10B21 cDNA RACE primer-4

<400> SEQUENCE: 20
cgaggtcgac gagtcccttc agc                                              23

<210> SEQ ID NO 21
<211> LENGTH: 24
<212> TYPE: DNA
<213> ORGANISM: Artificial Sequence
<220> FEATURE:
<223> OTHER INFORMATION: 2D14 cDNA RACE primer-1

<400> SEQUENCE: 21
ttagcaccgg cgtagaagtg atcg                                             24

<210> SEQ ID NO 22
<211> LENGTH: 23
<212> TYPE: DNA
<213> ORGANISM: Artificial Sequence
<220> FEATURE:
<223> OTHER INFORMATION: 2D14 cDNA RACE primer-2

<400> SEQUENCE: 22
gcatggaatg gaagggaggc agc                                              23

<210> SEQ ID NO 23
<211> LENGTH: 24
<212> TYPE: DNA
<213> ORGANISM: Artificial Sequence
<220> FEATURE:
<223> OTHER INFORMATION: 4H19 cDNA RACE primer-1

<400> SEQUENCE: 23
atacaacgca aggttcgctc actg                                             24

<210> SEQ ID NO 24
<211> LENGTH: 24
<212> TYPE: DNA
<213> ORGANISM: Artificial Sequence
<220> FEATURE:
<223> OTHER INFORMATION: 4H19 cDNA RACE primer-2

<400> SEQUENCE: 24
catgaccgct aaggatcagg agac                                             24

<210> SEQ ID NO 25
<211> LENGTH: 23
<212> TYPE: DNA
<213> ORGANISM: Artificial Sequence
<220> FEATURE:
<223> OTHER INFORMATION: 4H19 cDNA RACE primer-3

<400> SEQUENCE: 25
tctttcttgt gcaccgccga agc                                              23

<210> SEQ ID NO 26
```

```
<211> LENGTH: 23
<212> TYPE: DNA
<213> ORGANISM: Artificial Sequence
<220> FEATURE:
<223> OTHER INFORMATION: 4H19 cDNA RACE primer-4

<400> SEQUENCE: 26
tgcactcaca ccgccgatga tgg                                              23

<210> SEQ ID NO 27
<211> LENGTH: 27
<212> TYPE: DNA
<213> ORGANISM: Artificial Sequence
<220> FEATURE:
<223> OTHER INFORMATION: RACE adaptor primer

<400> SEQUENCE: 27
ccatcctaat acgactcact atagggc                                          27

<210> SEQ ID NO 28
<211> LENGTH: 30
<212> TYPE: DNA
<213> ORGANISM: Artificial Sequence
<220> FEATURE:
<223> OTHER INFORMATION: 22P8 genomic-DNA probe-1

<400> SEQUENCE: 28
tcctcgagct ctttcgtttg ctttggaaac                                       30

<210> SEQ ID NO 29
<211> LENGTH: 28
<212> TYPE: DNA
<213> ORGANISM: Artificial Sequence
<220> FEATURE:
<223> OTHER INFORMATION: 10B21 genomic-DNA probe-1

<400> SEQUENCE: 29
acaccaccag gttcacggcg aggaacag                                         28

<210> SEQ ID NO 30
<211> LENGTH: 28
<212> TYPE: DNA
<213> ORGANISM: Artificial Sequence
<220> FEATURE:
<223> OTHER INFORMATION: 10B21 genomic-DNA probe-2

<400> SEQUENCE: 30
gaggccttgc ctgccattgc tgcagagt                                         28

<210> SEQ ID NO 31
<211> LENGTH: 28
<212> TYPE: DNA
<213> ORGANISM: Artificial Sequence
<220> FEATURE:
<223> OTHER INFORMATION: 2D14 genomic-DNA probe-1

<400> SEQUENCE: 31
agcagttgga cgtgcaggcg ttggctac                                         28

<210> SEQ ID NO 32
<211> LENGTH: 27
<212> TYPE: DNA
<213> ORGANISM: Artificial Sequence
<220> FEATURE:
<223> OTHER INFORMATION: 2D14 genomic-DNA probe-2

<400> SEQUENCE: 32
```

```
aggttcacgg ccaggaacag cgcgaat                                              27

<210> SEQ ID NO 33
<211> LENGTH: 23
<212> TYPE: DNA
<213> ORGANISM: Artificial Sequence
<220> FEATURE:
<223> OTHER INFORMATION: 4H19 genomic-DNA probe-1

<400> SEQUENCE: 33
tctttcttgt gcaccgccga agc                                                  23

<210> SEQ ID NO 34
<211> LENGTH: 23
<212> TYPE: DNA
<213> ORGANISM: Artificial Sequence
<220> FEATURE:
<223> OTHER INFORMATION: 4H19 genomic-DNA probe-2

<400> SEQUENCE: 34
tgcactcaca ccgccgatga tgg                                                  23

<210> SEQ ID NO 35
<211> LENGTH: 22
<212> TYPE: DNA
<213> ORGANISM: Artificial Sequence
<220> FEATURE:
<223> OTHER INFORMATION: Genome Walker adaptor primer

<400> SEQUENCE: 35
gtaatacgac tcactatagg gc                                                   22

<210> SEQ ID NO 36
<211> LENGTH: 19
<212> TYPE: DNA
<213> ORGANISM: Artificial Sequence
<220> FEATURE:
<223> OTHER INFORMATION: 22P8GSP7 primer

<400> SEQUENCE: 36
actatagggc acgcgtggt                                                       19

<210> SEQ ID NO 37
<211> LENGTH: 37
<212> TYPE: DNA
<213> ORGANISM: Artificial Sequence
<220> FEATURE:
<223> OTHER INFORMATION: 5' lambda arm primer

<400> SEQUENCE: 37
ctgcttctca tagagtcttg cagacaaact gcgcaac                                   37

<210> SEQ ID NO 38
<211> LENGTH: 37
<212> TYPE: DNA
<213> ORGANISM: Artificial Sequence
<220> FEATURE:
<223> OTHER INFORMATION: 3' lambda arm primer

<400> SEQUENCE: 38
tgaacactcg tccgagaata acgagtggat ctgggtc                                   37

<210> SEQ ID NO 39
<211> LENGTH: 28
<212> TYPE: DNA
<213> ORGANISM: Artificial Sequence
<220> FEATURE:
```

<223> OTHER INFORMATION: 22P8DS1 primer

<400> SEQUENCE: 39
ttaagaacat gacggatgaa gaatcact                                          28

<210> SEQ ID NO 40
<211> LENGTH: 24
<212> TYPE: DNA
<213> ORGANISM: Artificial Sequence
<220> FEATURE:
<223> OTHER INFORMATION: 22P8GSP6 primer

<400> SEQUENCE: 40
tgatccgcag ttgcagcttg atcc                                              24

<210> SEQ ID NO 41
<211> LENGTH: 30
<212> TYPE: DNA
<213> ORGANISM: Artificial Sequence
<220> FEATURE:
<223> OTHER INFORMATION: 22P8DS5 primer

<400> SEQUENCE: 41
acaaaaaagc aggctgaaca tgacggatga                                        30

<210> SEQ ID NO 42
<211> LENGTH: 30
<212> TYPE: DNA
<213> ORGANISM: Artificial Sequence
<220> FEATURE:
<223> OTHER INFORMATION: 22P8DS9 primer

<400> SEQUENCE: 42
acaagaaagc tgggtcctcg agctctttcg                                        30

<210> SEQ ID NO 43
<211> LENGTH: 29
<212> TYPE: DNA
<213> ORGANISM: Artificial Sequence
<220> FEATURE:
<223> OTHER INFORMATION: attB1 primer

<400> SEQUENCE: 43
ggggacaagt ttgtacaaaa aagcaggct                                         29

<210> SEQ ID NO 44
<211> LENGTH: 29
<212> TYPE: DNA
<213> ORGANISM: Artificial Sequence
<220> FEATURE:
<223> OTHER INFORMATION: attB2 primer

<400> SEQUENCE: 44
ggggaccact ttgtacaaga aagctgggt                                         29

<210> SEQ ID NO 45
<211> LENGTH: 27
<212> TYPE: DNA
<213> ORGANISM: Artificial Sequence
<220> FEATURE:
<223> OTHER INFORMATION: 22P8DS3 primer

<400> SEQUENCE: 45
gcgtagttga agcttacaaa gttgcat                                           27

<210> SEQ ID NO 46

```
<211> LENGTH: 30
<212> TYPE: DNA
<213> ORGANISM: Artificial Sequence
<220> FEATURE:
<223> OTHER INFORMATION: 22P8DS7 primer

<400> SEQUENCE: 46
acaaaaaagc aggctgtagt tgaagcttac                                          30

<210> SEQ ID NO 47
<211> LENGTH: 26
<212> TYPE: DNA
<213> ORGANISM: Artificial Sequence
<220> FEATURE:
<223> OTHER INFORMATION: 10B21DS1 primer

<400> SEQUENCE: 47
gacggcccgg gctggtaaat tgactt                                              26

<210> SEQ ID NO 48
<211> LENGTH: 23
<212> TYPE: DNA
<213> ORGANISM: Artificial Sequence
<220> FEATURE:
<223> OTHER INFORMATION: 10B21GSP1 primer

<400> SEQUENCE: 48
catgctcgcg gctagcttag agg                                                 23

<210> SEQ ID NO 49
<211> LENGTH: 28
<212> TYPE: DNA
<213> ORGANISM: Artificial Sequence
<220> FEATURE:
<223> OTHER INFORMATION: 10B21DS3 primer

<400> SEQUENCE: 49
tggtaaattg actttgccta gtgttgga                                            28

<210> SEQ ID NO 50
<211> LENGTH: 23
<212> TYPE: DNA
<213> ORGANISM: Artificial Sequence
<220> FEATURE:
<223> OTHER INFORMATION: 10B21GSP2 primer

<400> SEQUENCE: 50
acagtcttgc cgcagtggtt gag                                                 23

<210> SEQ ID NO 51
<211> LENGTH: 30
<212> TYPE: DNA
<213> ORGANISM: Artificial Sequence
<220> FEATURE:
<223> OTHER INFORMATION: 10B21DS5 primer

<400> SEQUENCE: 51
acaaaaaagc aggcttgact ttgcctagtg                                          30

<210> SEQ ID NO 52
<211> LENGTH: 30
<212> TYPE: DNA
<213> ORGANISM: Artificial Sequence
<220> FEATURE:
<223> OTHER INFORMATION: 10B21DS7 primer

<400> SEQUENCE: 52
```

```
acaagaaagc tgggttgctg cagagtacag                                    30
```

<210> SEQ ID NO 53
<211> LENGTH: 27
<212> TYPE: DNA
<213> ORGANISM: Artificial Sequence
<220> FEATURE:
<223> OTHER INFORMATION: 2D14DS1 primer

<400> SEQUENCE: 53

```
atgggtttgc gggtatgggt agtggta                                       27
```

<210> SEQ ID NO 54
<211> LENGTH: 28
<212> TYPE: DNA
<213> ORGANISM: Artificial Sequence
<220> FEATURE:
<223> OTHER INFORMATION: 2D14GSP5 primer

<400> SEQUENCE: 54

```
acaccaccag gttcacggcg aggaacag                                      28
```

<210> SEQ ID NO 55
<211> LENGTH: 29
<212> TYPE: DNA
<213> ORGANISM: Artificial Sequence
<220> FEATURE:
<223> OTHER INFORMATION: 2D14DS3 primer

<400> SEQUENCE: 55

```
acaaaaaagc aggctgcggg tatgggtag                                     29
```

<210> SEQ ID NO 56
<211> LENGTH: 30
<212> TYPE: DNA
<213> ORGANISM: Artificial Sequence
<220> FEATURE:
<223> OTHER INFORMATION: 2D14DS5 primer

<400> SEQUENCE: 56

```
acaagaaagc tgggttgctc gatcacaaca                                    30
```

<210> SEQ ID NO 57
<211> LENGTH: 23
<212> TYPE: DNA
<213> ORGANISM: Artificial Sequence
<220> FEATURE:
<223> OTHER INFORMATION: 4H19GSP3 primer

<400> SEQUENCE: 57

```
tctttcttgt gcaccgccga agc                                           23
```

<210> SEQ ID NO 58
<211> LENGTH: 30
<212> TYPE: DNA
<213> ORGANISM: Artificial Sequence
<220> FEATURE:
<223> OTHER INFORMATION: 4H19profor primer

<400> SEQUENCE: 58

```
acccgataac gagttaacga tatgaactgg                                    30
```

<210> SEQ ID NO 59
<211> LENGTH: 23
<212> TYPE: DNA
<213> ORGANISM: Artificial Sequence
<220> FEATURE:

<223> OTHER INFORMATION: 4H19GSP4 primer

<400> SEQUENCE: 59
tgcactcaca ccgccgatga tgg                                           23

<210> SEQ ID NO 60
<211> LENGTH: 30
<212> TYPE: DNA
<213> ORGANISM: Artificial Sequence
<220> FEATURE:
<223> OTHER INFORMATION: 4H19proforB1 primer

<400> SEQUENCE: 60
acaaaaaagc aggctaacga tatgaactgg                                    30

<210> SEQ ID NO 61
<211> LENGTH: 30
<212> TYPE: DNA
<213> ORGANISM: Artificial Sequence
<220> FEATURE:
<223> OTHER INFORMATION: 4H19prorevB2 primer

<400> SEQUENCE: 61
acaagaaagc tgggtcttca cgagttcggt                                    30

<210> SEQ ID NO 62
<211> LENGTH: 30
<212> TYPE: DNA
<213> ORGANISM: Artificial Sequence
<220> FEATURE:
<223> OTHER INFORMATION: rfBclI primer

<400> SEQUENCE: 62
tgcccgtatg atcaacaagt ttgtacaaaa                                    30

<210> SEQ ID NO 63
<211> LENGTH: 30
<212> TYPE: DNA
<213> ORGANISM: Artificial Sequence
<220> FEATURE:
<223> OTHER INFORMATION: rfEcoRV primer

<400> SEQUENCE: 63
ccagaccgat atcaaccact ttgtacaaga                                    30

<210> SEQ ID NO 64
<211> LENGTH: 20
<212> TYPE: DNA
<213> ORGANISM: Artificial Sequence
<220> FEATURE:
<223> OTHER INFORMATION: MRS2 REV Primer

<400> SEQUENCE: 64
gctgcagagt acagaaagca                                               20

<210> SEQ ID NO 65
<211> LENGTH: 24
<212> TYPE: DNA
<213> ORGANISM: Artificial Sequence
<220> FEATURE:
<223> OTHER INFORMATION: MRS2-L FWD Primer

<400> SEQUENCE: 65
caccggcttg actttgccta gtgt                                          24

<210> SEQ ID NO 66

-continued

```
<211> LENGTH: 24
<212> TYPE: DNA
<213> ORGANISM: Artificial Sequence
<220> FEATURE:
<223> OTHER INFORMATION: MRS2-M FWD Primer

<400> SEQUENCE: 66
cacctgcgcg tgttcgtaga gttg                                              24

<210> SEQ ID NO 67
<211> LENGTH: 24
<212> TYPE: DNA
<213> ORGANISM: Artificial Sequence
<220> FEATURE:
<223> OTHER INFORMATION: MRS2-S FWD Primer

<400> SEQUENCE: 67
cacctgaact tgtgcacgtc attt                                              24
```